US012672774B2

(12) United States Patent
Skerswetat et al.

(10) Patent No.: US 12,672,774 B2
(45) Date of Patent: Jul. 7, 2026

(54) METHOD FOR VISUAL FUNCTION ASSESSMENT USING MULTISTABLE RIVALRY PARADIGMS

(71) Applicant: Northeastern University, Boston, MA (US)

(72) Inventors: Jan Skerswetat, Cambridge, MA (US); Peter John Bex, Concord, MA (US)

(73) Assignee: Northeastern University, Boston, MA (US)

( * ) Notice: Subject to any disclaimer, the term of this patent is extended or adjusted under 35 U.S.C. 154(b) by 393 days.

(21) Appl. No.: 18/274,253

(22) PCT Filed: Feb. 22, 2022

(86) PCT No.: PCT/US2022/017387
§ 371 (c)(1),
(2) Date: Jul. 26, 2023

(87) PCT Pub. No.: WO2022/178455
PCT Pub. Date: Aug. 25, 2022

(65) Prior Publication Data
US 2024/0081636 A1     Mar. 14, 2024

Related U.S. Application Data

(60) Provisional application No. 63/152,331, filed on Feb. 22, 2021.

(51) Int. Cl.
*A61B 3/08* (2006.01)
*A61B 5/00* (2006.01)
(52) U.S. Cl.
CPC .............. *A61B 3/08* (2013.01); *A61B 5/4088* (2013.01); *A61B 5/7475* (2013.01)

(58) Field of Classification Search
CPC ........... A61B 3/08; A61B 3/085; A61B 3/024; A61B 5/378; A61B 5/4088; A61B 5/7475;
(Continued)

(56) References Cited

U.S. PATENT DOCUMENTS

2009/0149769 A1     6/2009   Pettigrew
2014/0071251 A1     3/2014   Nakamura et al.
(Continued)

OTHER PUBLICATIONS

Kovács et al., "When the brain changes its mind: Interocular grouping during binocular rivalry", Proc. Natl. Acad. Sci. USA, vol. 93, pp. 15508-15511, Dec. 1996.
(Continued)

*Primary Examiner* — Thomas K Pham
*Assistant Examiner* — Justin W. Hustoft
(74) *Attorney, Agent, or Firm* — Adams & Reese LLP

(57) ABSTRACT

Testing methods for evaluating visual and neurological functions of a human or animal subject that involve conscious perception. The tests include a training phase, a practice phase, and a visual rivalry phase for detecting binocular rivalry or multistate competition. The design of the testing methods offers simple, rapidly administered, nonverbal visual testing with high time resolution and access to changing conscious perceptual states of the test subject. The methods also make possible the collection of a large amount of data in a short time for analysis of the subjects visual function and brain function, and can be used in the diagnosis of many medical conditions.

25 Claims, 26 Drawing Sheets

(58) Field of Classification Search
CPC ......... A61B 5/16; A61B 3/0058; A61B 5/742;
G02B 27/0093; G02B 27/0185; G06T
2207/30041; G06T 2207/10016; G06T
2207/10012; G16H 50/20; G16H 20/70;
A61H 2201/5043; A61H 2201/5007;
A61H 2201/501; A61H 2201/5025
USPC ................ 351/201, 246, 203, 240; 345/156;
348/51, 54; 715/771
See application file for complete search history.

(56)                  References Cited

U.S. PATENT DOCUMENTS

2017/0365101  A1*  12/2017  Samec ................... A61B 5/163
2020/0312038  A1   10/2020  Samec et al.

OTHER PUBLICATIONS

Wilson et al., "Dynamics of travelling waves in visual perception", Nature 412, pp. 907-910 (2001).
Lumer et al., "Neural Correlates of Perceptual Rivalry in the Human Brain", Science, vol. 280; pp. 1930-1934 (1998).
Harrad, R., "Psychophysics of suppression", Eye 10 ( Pt 2), pp. 270-273 (1996).
Tarita-Nistor, et al., "Intra- and inter-hemispheric processing during binocular rivalry in mild glaucoma", . PLoS One 15, pp. 1-16 (2020).
Robertson et al., "Slower Rate of Binocular Rivalry in Autism", The Journal of Neuroscience, (2013) • 33: pp. 16983-16991.
Liu et al, "Failure of Rivalry at Low Contrast: Evidence of a Suprathreshold Binocular Summation Process", Vision Res. 32, 1471-1479 (1992).
Skerswetat et al., "More superimposition for contrast-modulated than luminance-modulated stimuli during binocular rivalry", Vision Research, 142, (2018), pp. 40-51.

Sheynin et al., "Temporary monocular occlusion facilitates binocular fusion during rivalry", Journal of Vision (2019), 19, pp. 1-17.
Levelt, W.J.M., "On binocular rivalry", Soesterberg, Netherlands, (1965), 118 pages.
Zhou et al., "Perceptual dominance time distributions in multistable visual perception", Biol. Cybern. 90, pp. 256-263 (2004).
Brascamp et al., "The 'laws' of binocular rivalry: 50 years of Levelt's propositions", Vision Research 109 (2015), pp. 20-37.
Leopold et al., "Activity changes in early visual cortex reflect monkeys' percepts during binocular rivalry", Nature, 379, pp. 549-553 (1996).
Skerswetat et al., "Very few exclusive percepts for contrast-modulated stimuli during binocular rivalry", Vision Research, 121, pp. 10-22 (2016).
Hollins, M., "The effect of contrast on the completeness of binocular rivalry suppression", Perception & Psychophysics, (1980), 27, pp. 550-556.
Bossi et al., "A comparison of tests for quantifying sensory eye dominance", Vision Research, 153, pp. 60-69 (2018).
Klink et al., "Experience-Driven Plasticity in Binocular Vision", Current Biology, 20, pp. 1464-1469 (2010).
O'Shea et al., "The Effect of Spatial Frequency and Field Size on the Spread of Exclusive Visibility in Binocular Rivalry", Vision Research, 37, pp. 175-183 (1997).
Brascamp et al., "The time course of binocular rivalry reveals a fundamental role of noise", Journal of Vision (2006), 6, pp. 1244-1256.
Lew et al., "Stimulus dependence of interocular suppression", Scientific Reports, (2021), 11, 12 pages.
Blake et al., "Visual competition", National Reviews, Neuroscience (2002), vol. 3, pp. 1-11.
Logothetis et al., "What is rivalling during binocular rivalry?", Nature, vol. 380, Apr. 18, 1996, pp. 621-624.
Koch et al., "The Neuronal Basis of Visual Consciousness", Consciousness, pp. 1-35 (2004).
Handa et al., "Effects of Dominant and Nondominant Eyes in Binocular Rivalry", Optometry and Vision Science, vol. 81, No. 5, pp. 377-383 (2004).

* cited by examiner

Canonical states

Joystick movement

Physical stimulus changes

Regions of joystick space across subjects and conditions

Horizontal joystick space

Vertical joystick space

Low Contrast: Dominance of all joystick positions Left - right raw joystick data Low Contrast: Dominance of % exclusive visibility
Left - right exclusivity Low Contrast: Dominance of % superimposition
Left - right predominance superimposition

METHOD FOR VISUAL FUNCTION ASSESSMENT USING MULTISTABLE RIVALRY PARADIGMS

CROSS-REFERENCE TO RELATED APPLICATIONS

This application claims priority to U.S. Provisional Appl. No. 63/152,331, filed 22 Feb. 2021 and entitled "Method for Visual Function Assessment Using Binocular Rivalry", which is incorporated by reference herein in its entirety.

STATEMENT REGARDING FEDERALLY SPONSORED RESEARCH OR DEVELOPMENT

This invention was made with government support under Grant Numbers EY029713 and EY032162 awarded by the National Institutes of Health. The government has certain right in the invention.

BACKGROUND

The brain comprises multiple interdependent pathways that are structurally and functionally specialized and may be selectively affected across the lifespan. A family of multi-stable perceptual phenomena exists that cause an alternation of visual perception without a change of the physical enviorientation) from their counterpart. Adjacent binocular rivalry methods include interocular grouping (Diaz-Caneja, 1928; Kovács, Papathomas, Yang, & Feher, 1996), Flicker-Swap rivalry (Logothetis, Leopold, & Sheinberg, 1996), travelling-wave rivalry (Wilson, Blake, & Lee, 2001), and continuous flash suppression (Koch & Crick, 2004).

Binocular rivalry and other visual competition paradigms have been deployed as a clinical scientific tool in ophthalmology and optometry to determine and monitor eye dominance (Handa et al., 2004), as well as the behavior in clinically atypical groups such as amblyopia (Lunghi et al., 2019) or glaucoma (Tarita-Nistor, Samet, Trope, & González, 2019) (see Table 1). Clinical scientists in psychology and psychiatry use visual competition paradigms as a tool to objectively measure differences between neuro-typical and neuro-atypical populations such as autism spectrum condition (Freyberg, Robertson, & Baron-Cohen, 2015).

TABLE 1

Overview of clinical application and related references using binocular rivalry.

| Optometric applications | References | Psychological applications | References |
|---|---|---|---|
| Amblyopia/Strabismus | Adults: e.g. Schor et al, 1977 Children: Lunghi et al, 2016 | Bipolar disorder | e.g. Miller et al. 2003 |
| Eye dominance | e.g. Dieter et al., 2017 | Migraine | Wilkinson et al. 2008 |
| Keratoconus | Marella et al. 2021 | Personality traits | e.g. Antinori et al., 2017 |
| Cataract | Handa et al. 2006 | Autism | e.g. Robertson et al., 2013 |
| Contact lenses | Nitta et al, 2007 | hormonal influences | Sy et al. 2016 |
| Peripheral vision | Haun & Pelli, 2014 | Attention deficit syndrome | e.g. Jusyte et al. 2018 |
| Age-related macular degeneration | Tarita-Nistor et al., 2006 | Parkinson | Fujiwara et al., 2017 |
| Glaucoma | e.g. Tarita-Nistor et al., 2020 | Schizophrenia | e.g. Xiao, et al. 2018 | ronment. Visual competition paradigms have been used to search for the locus of perceptual changes in the conscious state of the mind (Koch & Crick, 2004; Logothetis et al., 1996; Lumer, Friston, & Rees, 1998).

One visual competition paradigm in particular, namely Binocular Rivalry (Blake & Logothetis, 2002; Porta, 1593), has become a popular tool to explore visual consciousness scientifically and quantitatively. In binocular rivalry paradigms, dissimilar images presented separately to each eye may compete for perceptual predominance, while the physical stimuli themselves remain unaltered. Conventional binocular rivalry generates perceptual alternation via stimuli that differ in at least one physical property (e.g., grating For more than 100 years, binocular rivalry has been measured by first describing to the participant what they are supposed to perceive and then asking the participant to make judgements of what they experience in every moment of a trial by pressing 2 to 5 buttons that match the closest to the descriptions provided by the test administrator. The resulting measures are an indication of which perceptual observations were experienced by the participant and for how long those experiences lasted. This earlier method lacks a validated individual introspection of perception, which is important because every individual experiences visual perception uniquely. It is also based on an assumption that the experiences described by the test designer represent all experiences for the participant, including neurologically atypical participants; this assumption is especially problematic. The standard method also uses a forced-choice procedure ("either-or"), which does not capture the dynamic, gradual nature of perceptual transitions during binocular rivalry. Further, the standard method does not capture all types of mixed perceptual experiences reported in the literature, nor does it capture mixed states that blend into another dynamically. The standard method also does not measure the transition probability of each change, nor does it weight the interaction of each state with another, which is important for the computation required for diagnosis of brain events. Finally, the results generated during a one minute trial using the standard method consists typically of 15-30 data points, which are too sparse and too few in numbers to capture dynamic perceptual speed and velocity of perceptual changes across time.

In terms of the visual system, screening of different visual structures is essential for both clinical and basic scientists. Comprehensive vision screening ideally requires the administration of multiple tests that assess the integrity of different visual structures and pathways. However, in practice, combined limitations on the time available to clinicians and basic scientists and on the burden of assessment on subjects, severely limit the number of tests that can be administered. These factors can be frustrating for participants and may confound attention, learning and memory effects with visual function deficits. These pressures have led to compromises in the number and duration of tests that are administered, with the risk that the vision screening is inaccurate (due to noisy or under-constrained data) or incomplete (because only a subset of tests is administered). From a psychological/ psychiatric perspective, clinicians use subjective measures, i.e. interviews and questionnaire data, to screen and differentiate neuro-typical from neuro-atypical patients. These qualitative data rely on individual user experience and show variance across examiners, causing repeatability issues that may amount to incorrect diagnosis. Further issues are language barriers that make the interpretation of such data difficult and troublesome. From a neuro-scientific/surgical perspective, scientists/surgeons use visual tests to probe functioning after brain damage or before/after treatment of neuro-ophthalmological interventions. However, the assessment of those data lacks validated introspection i.e. validated knowledge of an individual's perceptual experience, which has important consequences when diagnosing either damage or treatment of brain structure: a) the lack of introspection hinders the drawing of a clear link between visual conscious experience and structural measures of brain activity and b) may cause inaccurate data as the test-retest variability may be larger than changes caused by damage and/or treatment.

SUMMARY

The present technology provides tests for evaluating visual functions that involve conscious perceptions. The tests include at least three phases: (i) a training phase in which the test subject explores using an input device to change displayed physical images that simulate a perception state, which is a perceived aspect of the displayed image that may mimic rivalry between images, or may mimic multistate competition, which is a series of perceptual changes between two or more distinct perceptual states within the mind of the viewer; (ii) a practice phase in which the subject is shown a series of images that simulate rivalry or multistate competition; and (iii) an actual rivalry or multistate competition phase in which the subject is shown images that induce rivalry or multistate competition in the subject's visual perception.

The methods of the present technology offer simplified nonverbal visual testing compared to previous methods, with high time resolution of changing conscious perceptual states by the test subject. The methods also make possible the collection of a large amount of data in a short time for analysis of the subject's visual function and brain function, and can be used in the diagnosis of many medical conditions.

The technology also can be summarized as including the following features.

1. A method of testing a visual function comprising conscious visual perception, the method comprising the steps of:
   (a) providing a test system for presenting a series of images to a subject and receiving physical responses from the subject, the system comprising a stereoscopic or non-stereoscopic viewing device, an input device for continuous physical input in response to physical changes of a displayed image or a perceptual change of unaltered physical images by the subject, a data storage device operative to receive and store data from the input device, and an analysis device configured to analyze the stored data;
   (b) displaying to the subject a series of images using the viewing device, wherein the images present a pair of individual images simultaneously to each eye or a multi-stable non-stereoscopic image, in response to use of the input device by the subject, so as to train the subject to input perceptual states induced by the displayed images using the input device;
   (c) displaying to the subject using the viewing device a series of physically changing images, wherein the images present a simulated combination of a pair of individual images, while the subject uses the input device to report said perceptual states continuously, and while data from the input device are stored in the data storage device;
   (d) presenting to the subject dichoptically a series of binocular images using the stereoscopic viewing device while the subject uses the input device to report said perceptual states, and while data from the input device are stored in the data storage device; and
   (e) analyzing visual functions of the subject using data reported by the subject in (c) and (d) using the analysis device.
2. The method of feature 1, wherein the method further comprises:
   (f) presenting to the subject non-dichoptically a series of binocular images using the stereoscopic viewing device, wherein the series of binocular images simulate dynamically the perceived aspects reported by the subject in (d), while the subject uses the input device to again report said perceptual states induced by dynamically changing, physical images based on the subject's responses in (d), and while data from the input device are stored in the data storage device; and
   (g) analyzing the agreement between subject's responses in (d) and (f) using the analysis device, wherein said differences provide a measure of test-retest variability of the subject.
3. The method of any of the preceding features, wherein the series of images comprise lines, curves, grating patterns, geometric patterns, faces, or objects, which can be presented statically or in motion.

4. The method of any of the preceding features, wherein a stereoscopic viewing device is used, and the stereoscopic viewing device comprises a head-mounted projection display, a 3D display system, a computer screen, or a display screen of a mobile device or tablet.

5. The method of any of the preceding features, wherein the input device is a joystick, virtual reality flight stick, hand tracker, trackball, computer mouse, touchpad, or touch-sensitive screen.

6. The method of any of the preceding features, wherein the input device provides a series of XY coordinates representative of user input as a function of time.

7. The method of any of the preceding features, wherein the subject is unaware of a transition from step (c) to step (d).

8. The methods of any of the preceding features, wherein the analyzing of step (d) comprises estimation of most likely boundaries of said perceptual states using a Gaussian mixture model, k-means cluster analysis, a support vector machine (SVM), or other machine learning approach to classify said perceptual states.

9. The methods of any of the preceding features, wherein the analyzing of step (e) comprises creation of maps of introspection, and comparison of sizes of the maps corresponding to said perceptual states within and between subject as a validated measure for introspection.

10. The methods of any of the preceding features, wherein the analyzing of step (e) comprises evaluating the mean and relative proportions of each perceptual state, the rate of perceptual state changes, the eye dominance scores in total and for each perceptual state, weighted transition probabilities using machine learning, such as a Hidden-Markov Model algorithm, analyzing the subtypes of joystick changes and thus perceptual changes evaluating the perceptual velocity across perceptual states and within mixed states, and perceptual states related to neuro-receptive field interactions.

11. The method of any of the preceding features, wherein said visual function comprising conscious visual perception is a form of rivalry selected from the group consisting of classic binocular rivalry, interocular grouping, flicker-swap rivalry, continuous flash suppression, and travelling-wave rivalry.

12. The method of feature 11, wherein the visual function is classic binocular rivalry, and the static or moving rivaling binocular images presented in step (d) comprise pairs of images, one for display to a left eye and the other for display to a right eye, and wherein the images of the pair are distinguishable by the subject as exclusively left eye perceptual states, exclusively right eye perceptual states, piecemeal perception as combination of the left and right eye perceptual states, equal superimposition perception of left and right eye perceptual states, left-predominant superimposition perception of left and right eye perceptual states, or right-predominant superimposition perception of left and right eye perceptual states.

13. The method of feature 12, wherein the non-rivaling binocular images presented to the subject in steps (b) and (c) simulate the rivalry depicted in step (d) by being distinguishable by the subject as representing exclusively left eye perceptual states, exclusively right eye perceptual states, piecemeal combination of the left and right eye perceptual states, equal superimposition of left and right eye perceptual states, left-predominant superimposition of left and right eye perceptual states, or right-predominant superimposition of left and right eye perceptual states.

14. The method of any of features 11-13, wherein said perceptual states comprise presence or absence of a form of rivalry, type of rivalry, response time of perceived change in rivalry, and conscious visual perception.

15. The method of any of the preceding features, wherein the analysis of step (e) provides an indication of visual cognitive functioning, a monocular visual function, or a binocular visual function.

16. The method of any of the preceding features, wherein perceptual state, stimulus property, and primary brain processing site are according to any portion of the table below

| Perceptual state | Stimulus property | Primary processing site |
|---|---|---|
| Exclusive visibility | Static gratings | Early visual cortex V1 |
| | Objects | Para hippocampal place area (PPA) |
| | Faces | Fusiform area (FFA) |
| | Moving dots | Middle temporal (MT) area |
| Piecemeal perception | | Early visual cortex |
| Superimposed perception | | Binocular regions early visual cortex (Layer 4 V1, V2) |
| Interocularly grouped perception | | Early visual cortex V1 and V2 binocular |
| Traveling wave perception | | Early visual cortex V1. |

17. The method of any of the preceding features that is used as part of a healthcare diagnosis, a neuro-behavioral test, an ophthalmological test, an optometric test, a visual consciousness measurement, a visual function test, as a diagnostic test for a visual impairment, or as a test of an outcome of a vision-related treatment or surgery.

18. The method of any of the preceding features, wherein said perception state in induced by viewing an interocular grouping, ambiguous figures, continuous flash suppression, an afterimage, or a face perception task.

19. The method of any of the preceding features, wherein the method provides diagnosis, prognosis, or treatment outcome evaluation related to ophthalmic disorders such as cataract surgery, amblyopia, age-related macular degeneration, glaucoma, intraocular lens implantation, contact lens or spectacle prescription, and neurological disorders and damages such as traumatic brain injury, autism, attention deficit disorder, depression, bipolar disorder, or schizophrenia, Alzheimer disease, dyslexia.

20. A system for conducting a binocular rivalry test according to any of the preceding features, the system comprising:

a stereoscopic or viewing device configured for displaying binocular images to a test subject;

an input device for input of responses from the test subject;

a data storage device configured for storing input data from the input device and test parameters; and an analysis device configured for analyzing one or more visual functions or perceptions of the subject.

21. The system of feature 20, wherein the stereoscopic viewing device comprises a head-mounted projection display, a 3D display system, a computer screen, or a display screen of a mobile device or tablet.

22. The system of feature 20 or feature 21, wherein the input device is a joystick, virtual reality flight stick, hand tracker, trackball, computer mouse, touchpad, or touch-sensitive screen.

23. The system of any of features 20-22, wherein the data storage device and the analysis device are both present in a single computer, laptop, notebook, or mobile phone.

24. The system of any of feature 20-22, wherein the data storage device and the analysis device are at separate locations, the system further comprising a transmitter operative to send data from the data storage device to the analysis device.

25. The system of any of features 20-24, further comprising a processor and memory comprising instructions for carrying out the method of any of features 1-19 or any portion thereof.

BRIEF DESCRIPTION OF THE DRAWINGS

FIG. 5D depicts the Gamma function (dashed curve), the histogram, and the following parameters: shape and scale parameter of the Gamma function, number of events N, coefficient of determination R2, area under the Gamma function curve (AUC) from 0.18 to 4 along x axis, X/Y peak of the Gamma function.

FIG. 7A shows the scheme of classification space and a hypothetical joystick indication with labeled velocity markers. FIG. 7B show an example of trial state changes (solid line with discrete state near middle of figure) across a trial. Trial mean (straight line at bottom of figure), SD (dashed line) and the actual velocity changes (blue line) are depicted. FIG. 7C depicts the relative proportions and FIG. 7D the absolute number of events of the four change categories, namely Stable perception, rivalry tremor, micro-saccades, and saccades averaged across trials and contrast conditions. One-way ANOVAs and significant differences found via planned comparisons are depicted as well (*p<0.5, p<0.01, *p<0.001). FIG. 7E is a colormap that visualizes the (lack of) change of velocity for all trials, conditions, and participants. FIG. 7F presents a Fast-Fourier-Transform of velocity for each trial, conditions and participant (participants shown by different shades).

DETAILED DESCRIPTION

Figure 1:
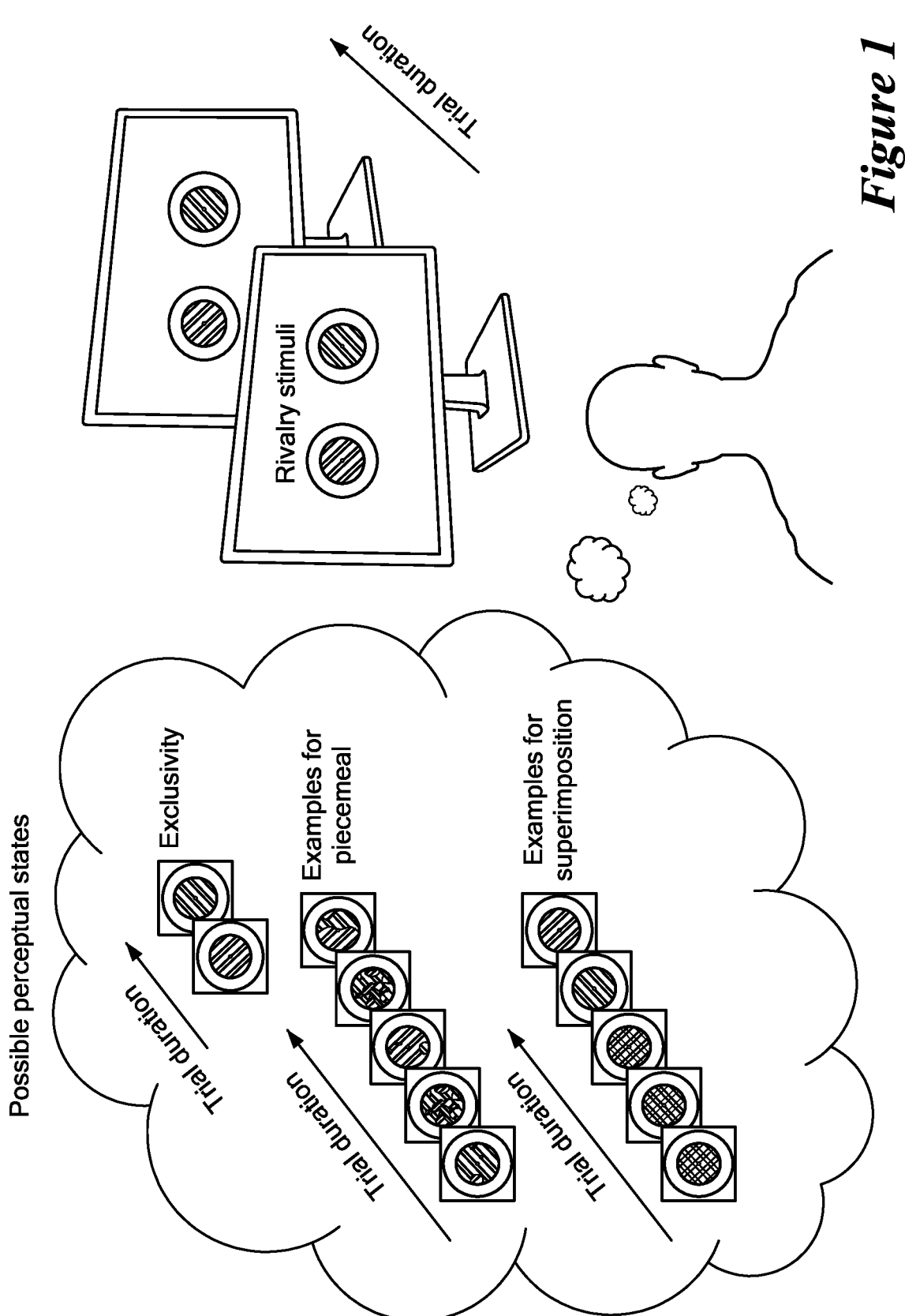
FIG. 1 shows a schematic illustration of binocular rivalry experiences. Dissimilar images, here two gratings tilted in different directions (shown at right side of figure), are presented separately to each eye, causing an ongoing change of perception (left side of figure) between two "exclusive" perceived grating orientations, or among various types of "piecemeal" and "superimposed" perceptions. These experiences alternate in a random order in an ongoing fashion across viewing time for a single observer.

The present technology includes a novel 4-phase-method that dynamically tracks and validates visual experiences, allowing novel measurements of visual consciousness and visual suppression dynamics, taking advantage of a phenomenon called binocular rivalry. Here, incompatible images are presented separately to the eyes (see FIG. 1) causing an ongoing alternation of various perceptual experiences (FIG. 1) since those images cannot be merged to a coherent impression. The test is called InFoRM (Indicate-Follow-Replay-Me): Rivalry and requires participants to indicate their perception of a physical binocular stimulus (Phase 1: Indicate) via joystick (or other data input device) while looking on a screen. The participants explore the change of the presented stimulus caused by their own joystick movement (FIG. 2), thereby exploring and learning the joystick-stimulus behavior. In Phase 2 (Follow), participants follow dynamically via joystick ongoing changes of the physical binocular stimulus. The stimuli presented in this phase mimic actual rivalry trials and serve as training for the participant in the report paradigm and most importantly also validate their own indication generated during Phase 1 for principal states that may occur during binocular rivalry. In Phase 3 (Rival), participants move the input device to report their experience of perceptual-rivalry induced via dichoptic stimulus presentation. As the task has not changed, the participant remains blind to the change of condition from binocular to dichoptic stimulus presentation. In Phase 4: Replay-Me, participants follow again physically changing binocular stimuli using the joystick, but this time the physical changes are generated by the responses generated by the participant themself during Phase 3, which validate their individual perceptual-state-spaces.

InFoRM Rivalry is a 4-phase method that uses a joystick to collect human participant data and Gaussian Mixture Modeling to classify canonical perceptual states of participant's self-generated data. This approach validates and customizes the task, trains individuals to respond to simulated rivalry dynamics, collects actual rivalry data, and validates those responses while keeping the naive participant blind to the actual onset of the rivalry task (Phase 3). Stimuli can be varied, using simple images such as gratings (FIG. 1) or more complex images such as face or object images. This allows the investigation of various brain regions and also allows the user to adapt the stimuli to the particular population, i.e. children, adults, people with different culture backgrounds and different literacy levels.

A conventional stereoscopic system is required to present binocular-non-rivaling and dichoptic-rivaling stimuli, leaving participants condition-blinded. Participants are instructed to move a joystick to actively control the physical stimuli or to provide a continuous output of perceptual experience. Other data input devices could be employed, including a touch pad, virtual reality flight stick, hand tracker or mouse. Perceptual-state-space is controlled with thresholded band-pass filtered noise: the parameters controlling the different perceptual experiences are mapped onto the joystick axes: for example fPeak(#areas) can be controlled on the vertical axis; and threshold(proportion for each image) onto the horizontal axis. The joystick coordinates (XY) are measured during each frame of the monitor, e.g. 60 Hz, resulting in 3600 data points per standard rivalry trial duration. The physical changes of the stimulus that simulate (Phase 2) or replay (Phase 4) actual rivalry experience are updated in real-time based on current, or pre-recorded XY response coordinates, providing a straight mathematical comparison between physical stimulus on screen and perceptual experience indicated via joystick (or other data input device).

Figure 3:
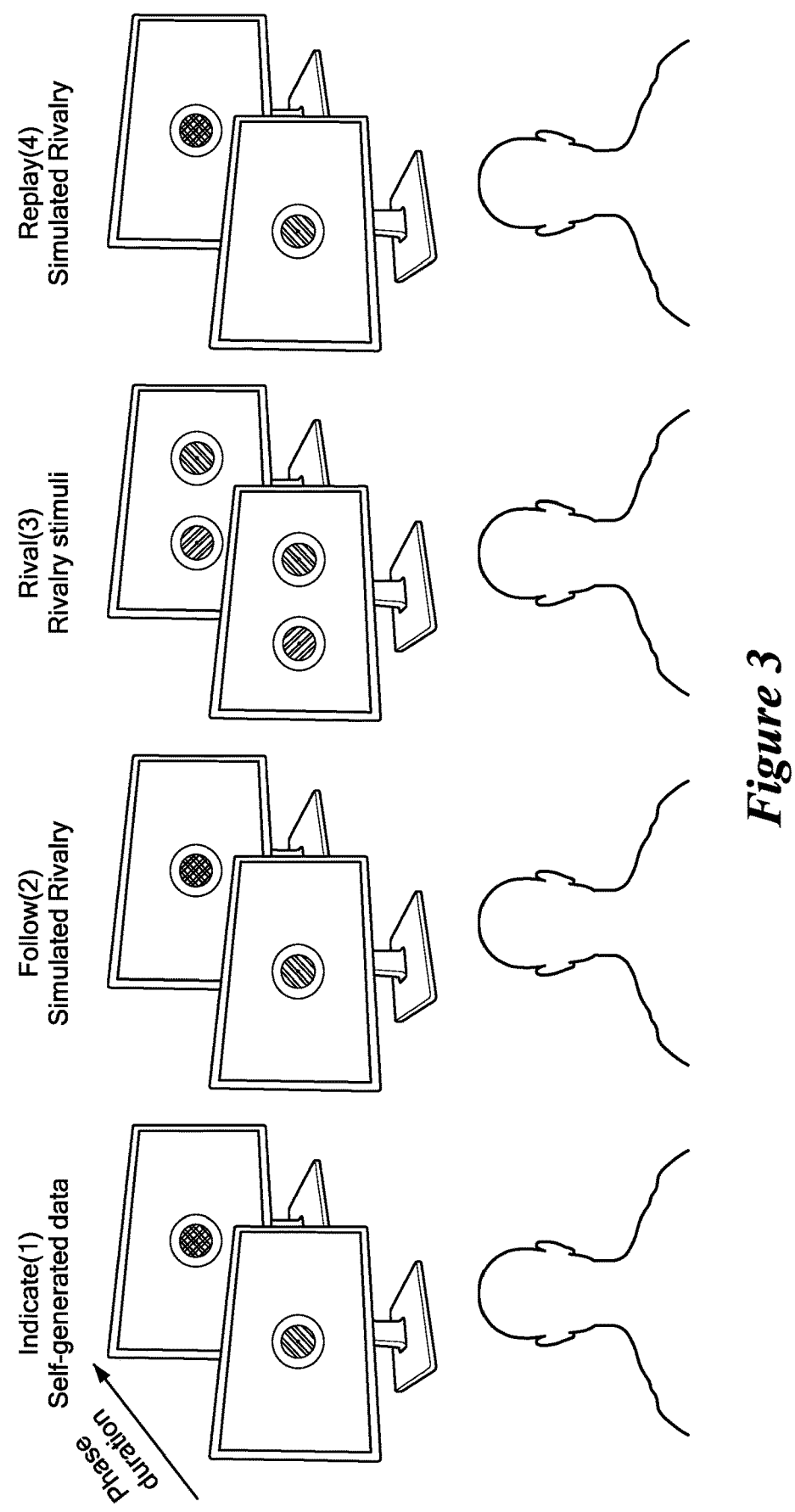
FIG. 3 illustrates four phases of the perceived rivalry detection method. Phase 1 ("Indicate") asks the subject to explore the perceptual space by moving the joystick in all directions and observing the relationship between the joystick and the appearance of the physical binocular stimulus (binocular image—same displayed for each eye). The subject is asked to generate the canonical states "exclusive left", "exclusive right", "piecemeal", "equal superimposition", "left-predominant superimposition", "right-predominant superimposition" to demonstrate their understanding of this relationship. Phase 2 ("Follow") asks the subject to follow dynamic changes of a physical stimulus (displayed binocular image—same displayed for each eye) as accurately and immediately as possible to confirm that they understand how the joystick is used to report their perceptual experience for known stimuli. Phase 3 ("Rival") asks the subject to do the same as for Phase 2; however, here two static images are presented dichoptically (different image to each eye), which results in binocular rivalry experiences by the subject, which the subject records by positioning the joystick according to the same pattern learned in Phase 1 and practiced in Phase 2. The different nature of the task in Phase 3 is not revealed to the subject. In Phase 3, any changes registered by the subject are generated by the subject's visual system, spontaneously changing over time, and not by the testing apparatus or its program. In Phase 4 ("Replay") the subject is asked again to continue the same task as for Phase 3; however, images are displayed (same to each eye) which replicate the images indicated by the subject as a function of time during Phase 3. The stimulus changes are generated by using a replay of the subject's joystick coordinates as a function of time during Phase 3.
Figure 4A:
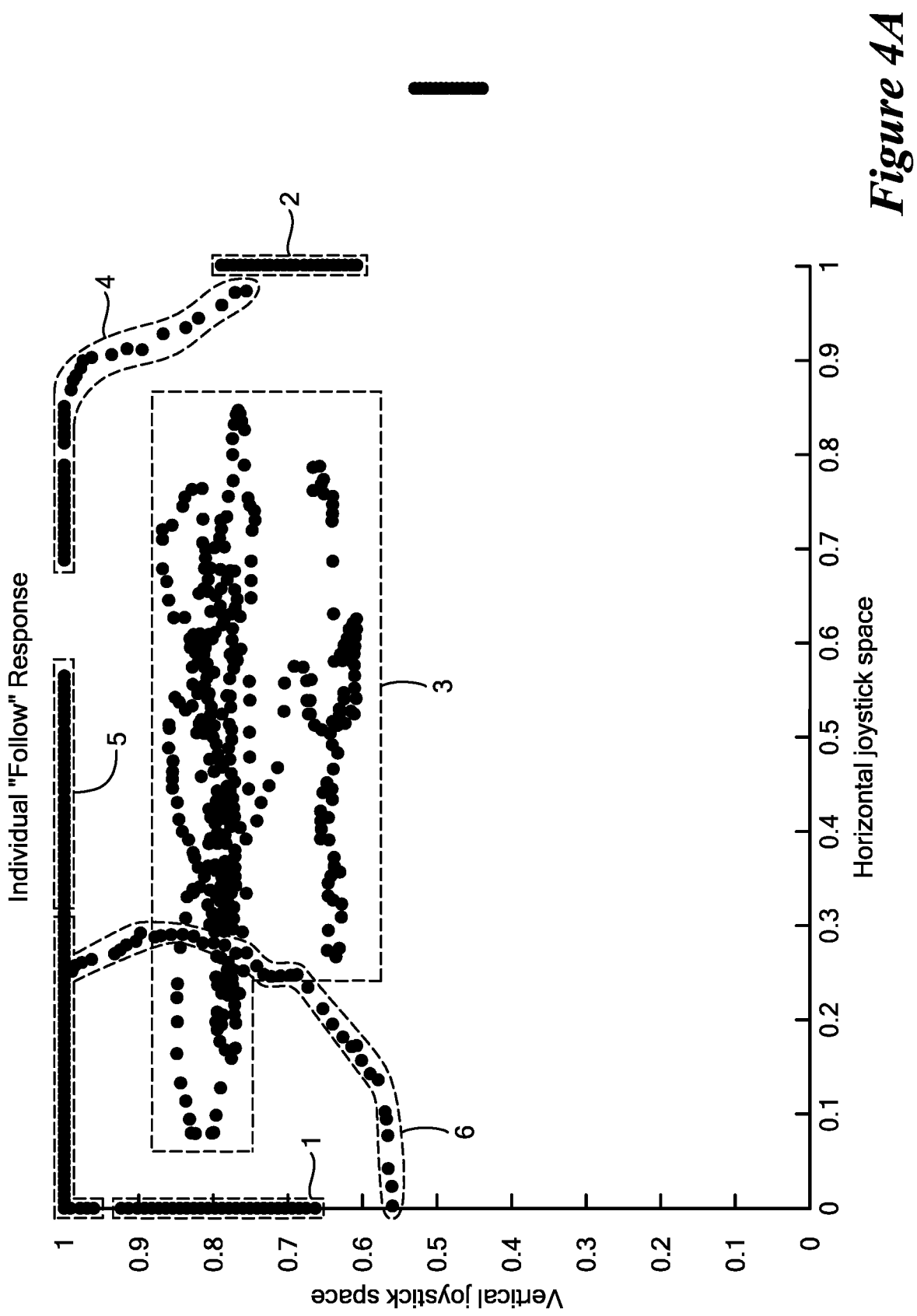
FIG. 4A shows the vertical (y-axis) and horizontal (x-axis) coordinates of a subject's joystick position as a function of time during Phase 1 (Follow). All data gathered during Phase 1 were extracted, and a Gaussian Mixture Model was used to determine the likelihood of each state to occur (shown in FIG. 4B) across the joystick area; the maximum likelihood for each state were used to determine the boundaries between canonical states. Such classification maps can be averaged across a number of users or trials (FIG. 4C displays the average over 28 subjects).
Figure 4B:
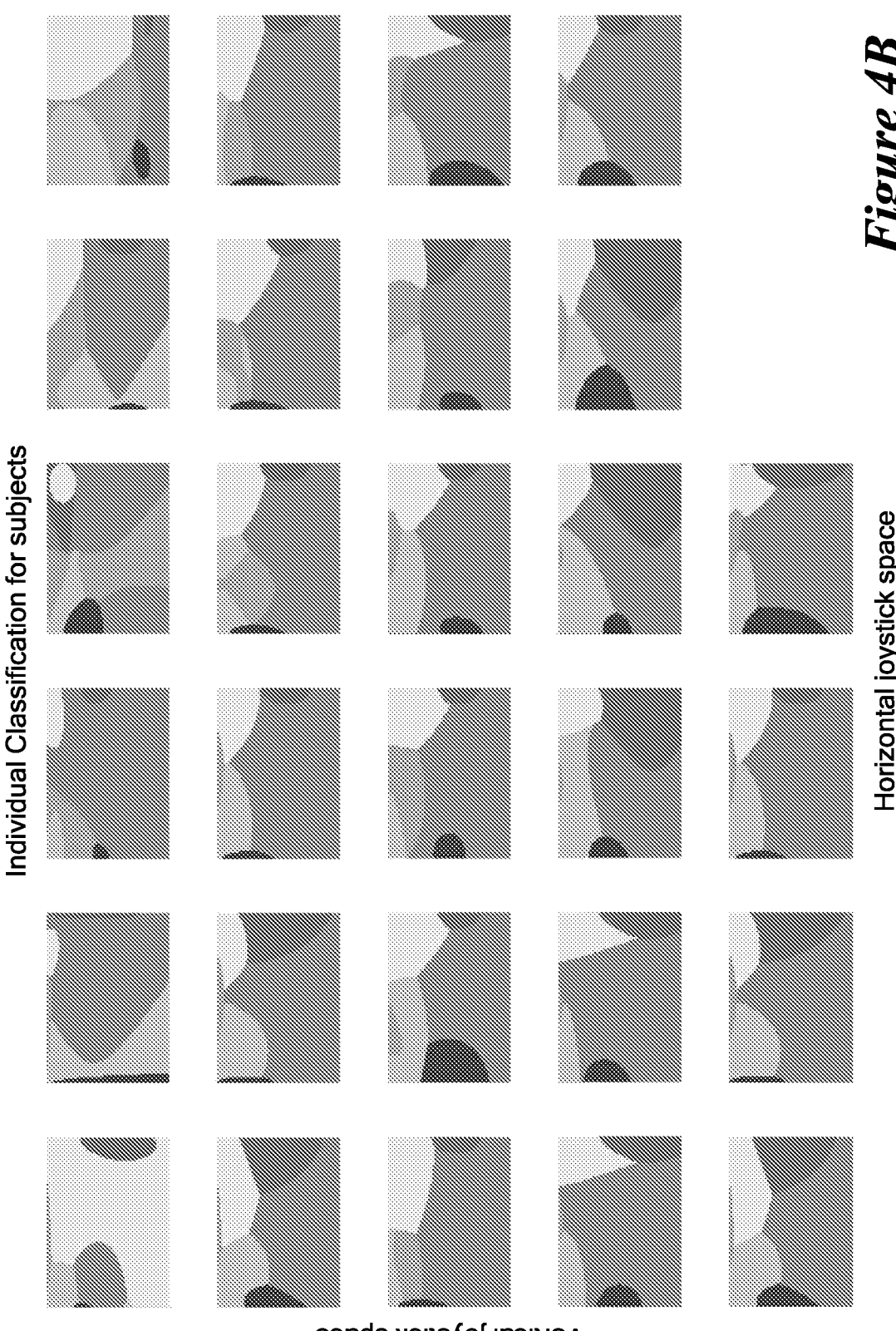
In FIG. 4C, area 1 indicates "exclusive left", area 2 indicates "piecemeal", area 3 indicates "exclusive right", area 4 indicates "left-predominant superimposition", area 5 indicates "equal superimposition", and area 6 indicates "right-predominant superimposition".
Figure 4C:
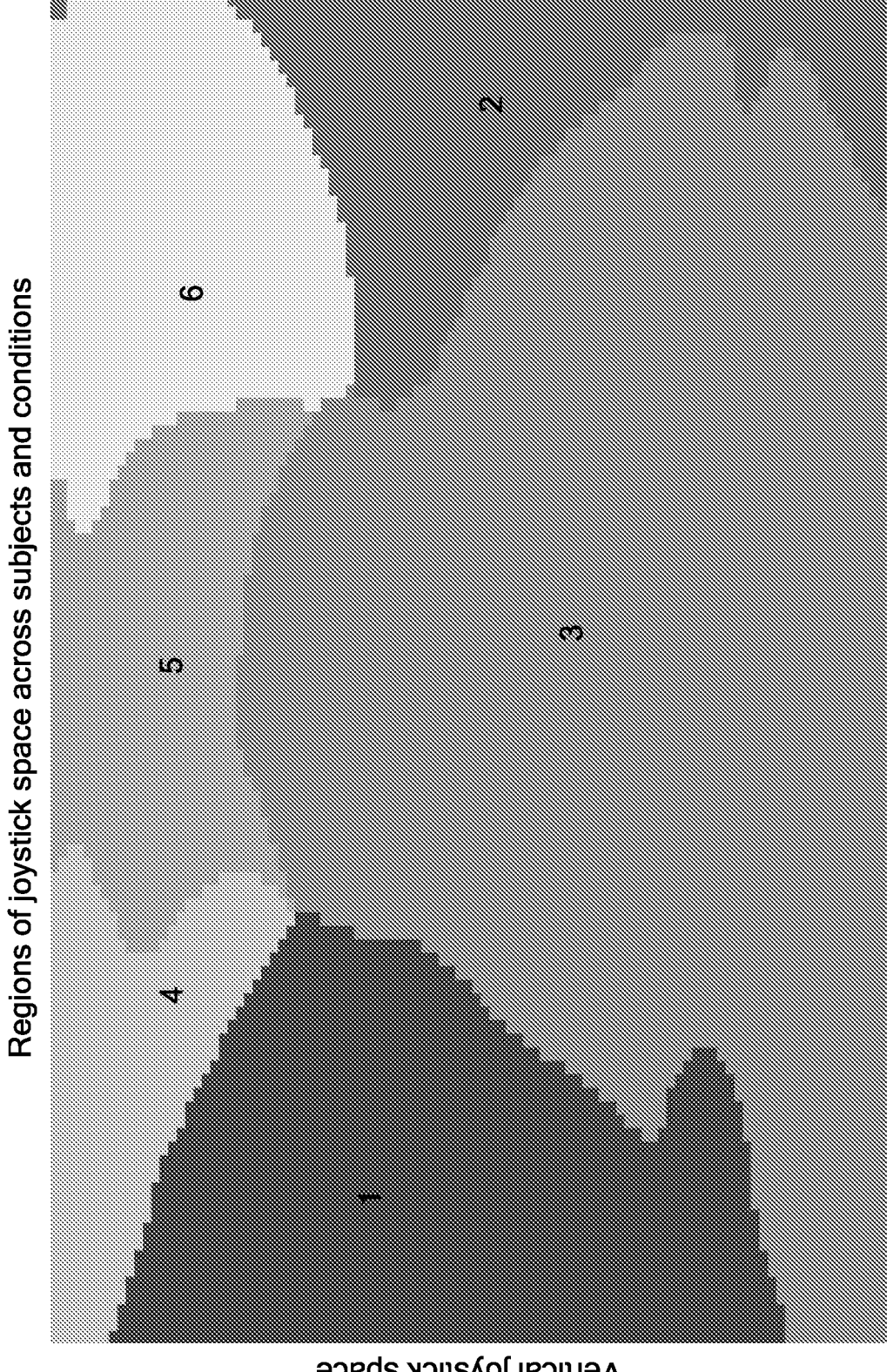

Each InFoRM Rivalry phase is depicted in FIG. 3 and works as follows:

Phase 1 "Indicate"

Figure 2:
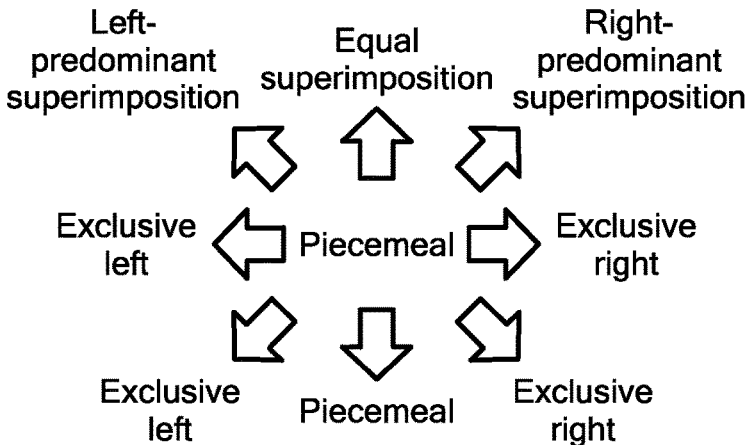
FIG. 2 Illustrates the relationship between perceived stimulus and subject-assigned joystick position. In Stage 1 of the method (Indicate), the canonical states (left side of figure) can be displayed instantaneously (right side of figure, same image to both eyes) by moving the joystick to the corresponding position (middle of figure). Note that the images on the right are examples of principal perceptual states. Each slight joystick movement away from its cardinal (central) position (piecemeal) will affect the appearance of the physical image in a graded manner.
Figure 2:
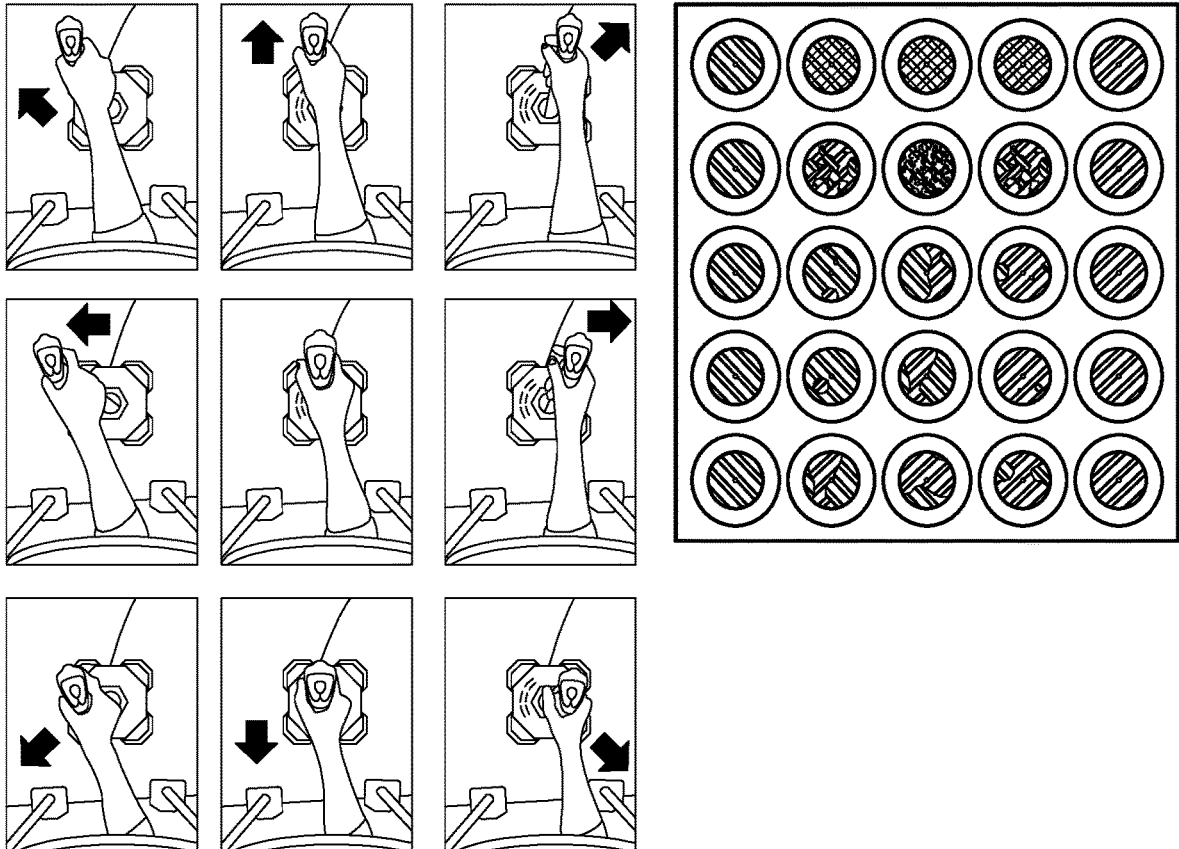

During Indicate, participants explore the stimulus-space for defined time, e.g. 60 sec, and move the data input device to modify binocular-non-rivaling stimuli in real-time and simulate six canonical rivalry states (FIG. 2).

Phase 2 "Follow"

During Follow, participants match perceptual reports for physically changing binocular-non-rivaling-stimuli in author-created rivalry trials and self-generated trials illustrating canonical rivalry states from Indicate. The responses to the self-generated Indicate data during Follow can be classified as 2 or more classic responses using Gaussian mixture models (see illustration of process in FIG. 3), to calculate standard measures of binocular rivalry for comparison with results gained by conventional method. Other unsupervised machine learning methods, such as Support Vector Machines and K-Means cluster analysis may be used to classify the perceptual response space. Furthermore, cluster analysis can be used to generate an unbiased estimate of the number of unique perceptual states experienced by different participant populations.

Phase 3 "Rival"

During Rival, participants reported their perception during eight 60 sec-trials of binocular rivalry. Here static images are presented dichoptically, but remain unchanged. Only the perceptual experiences may constantly change across a trial (FIG. 1). Phase 3 is interchangeable and can be applied to binocular rivalry, as demonstrated here, but also for other visual functions such as interocular grouping, ambiguous figures, continuous flash suppression, studies of afterimages, face perception tasks etc., all of which may provide unique insights to the conscious experiences of different neurological populations. The resulting continuous response data can then be used to calculate both standard measures of rivalry for comparison, but also novel measures of weighted transition probabilities using machine learning technology, i.e. Hidden-Markov Model algorithms, fast Fourier transformation for analysis of perceptual speed and velocity as well as perceptual states that may be generated by computational models of neuro-receptive field interactions.

Phase 4 "Replay"

During Replay, participants' responses during Rival dichoptic-trials are used to generate physically changing binocular stimuli, which validates the individual perceptual-state-space reported in Phase 3. Specifically, the XY coordinates generated during Phase 3 with the input device (e.g. joystick) will be used as XY coordinates for the physical variation of the stimulus, thereby replaying the experience during Rival. The agreement between participants joystick indications during Phases 3 and 4 is therefore a direct validation of response accuracy, both in terms of temporal precision and in terms of states, giving insight into the test-retest variability of each individual.

The present technology includes the following novel and unusual features:

i) InFoRM Rivalry measures dynamically a continuous output of all possible stimulus-driven perceptual states.

ii) InFoRM Rivalry creates a much larger raw data pool (e.g. 3600 data points) compared to (~25 data points collected with standard button-press paradigms) using conventional methods in the same time-frame, which allows novel analysis of perceptual dynamics, with higher temporal resolution, and raises the possibility of decreasing test duration.

iii) InFoRM Rivalry validates individual introspection and validates rivalry experience, ensures high test-reliability and identifies malingering because subjects could not reliably reproduce data from their previous fabricated reports.

iv) InFoRM allows flexible use of different stimulus types and other visual functions, essential for testing neuro-visual and ophthalmological functions and targeting different levels of the visual cognition system.

v) The dynamic, intuitive, and fast task (i.e., 4 minutes to completion) makes InFoRM Rivalry appealing for population with a short attention span, such as young children, people with attention deficits or elderly people.

The present technology offers the following advantages over previous technology:

i) InFoRM Rivalry is the only method that individually measures and validates introspection of a participant's conscious visual experience.

ii) InFoRM Rivalry leaves the participant blind to the actual task, so they are unaware of validation and testing phases of the test.

iii) InFoRM Rivalry has in-built validation of rivalry experience as default, other approaches assume a limited number of possible states that may not be relevant for neurologically atypical participants.

iv) InFoRM Rivalry gathers much more continuous raw data compared to current methods, allowing novel analysis of dynamic visual functions that cannot be generated with any other currently known rivalry method.

The present technology can be used in the following ways:

i) InFoRM Rivalry can be used as an endpoint in the ophthalmological clinic to monitor treatments that affect binocular vision, such as cataract surgery, amblyopia, age-related macular degeneration, glaucoma. Numerous drug companies and hospitals are seeking new clinical trial endpoints in this area.

ii) InFoRM Rivalry can be used as an endpoint for optometric correction, e.g. after intraocular lens, contact lens or spectacle prescription. Numerous lens manufactures are seeking new clinical trial endpoints in this area.

iii) InFoRM Rivalry can be used to screen and monitor for neurological conditions such as traumatic brain injury, autism, depression, bipolar disorder, schizophrenia etc. Clinicians worldwide seek sensitive, objective diagnostic tools, rather than relying only on interview and questionnaire findings. Numerous drug discovery companies are seeking new clinical trial endpoints in this area.

iv) InFoRM Rivalry can be used as a neuroscientific tool to investigate neural correlates of visual perception in the brain. Numerous neuroscience labs around the world are seeking new ways of investigating visual consciousness.

EXAMPLES

Example 1. Validation of InFoRM Rivalry Method for Testing Binocular Rivalry

The experiments were carried out in the facilities of the Northeastern University, Boston, MA. Written and verbal information about the project were provided in advance to the participants and they gave written informed consent before taking part. Ethics approval to conduct the experiments on human participants was in line with the ethical principles of the Helsinki declaration of 1975 and ethics board of the Northeastern University. Participants were recruited from Translational vision laboratory as well as from the undergraduate population at Northeastern University, Boston. Undergraduates received course credit towards the completion of their Introductory Psychology course in exchange for their participation.

Equipment

Stimuli were presented on a LG 3D monitor with a framerate of 60 Hz at a viewing distance of 150 cm. The participants wore radially-polarized LG cinema 3D glasses (AG-F310) and provided responses with a Logitech Extreme™ 3D pro (Logitech Europe S.A.) joystick.

Stimuli

Matlab (2019b) software was used to generate all the code for the experiments in combination with Psychtoolbox version 3.0 (Brainard, 1997; Pelli, 1997). Prior the experiment, the monitor was gamma-corrected using a Photo Research SpectraScan 655 (Norway) spectrophotometer. Crosstalk was minimized with Psychtoolbox's StereoCrosstalkReduction and SubtractOther routines to minimize the subjective visibility of a 100% contrast 2 c/deg sine grating presented to one eye that was patched and a mean luminance field presented to the other eye that was used to judge crosstalk.

Non Dichoptic Grating Stimuli

The circular aperture of sinewave gratings had 2° diameters, and 2 cycles/° spatial frequency, which provides high perceptual alternation between the stimuli thus favors exclusive over mixed perception under using a 3 choice rivalry task (O'Shea, Sims, & Govan, 1997). The gratings were obliquely (135° and 45°) orientated. The Michaelson-contrast conditions for the stimuli were bilaterally 10% or 50%, or unilaterally 10% vs 50%. Those contrast levels were chosen because it is known that lowering the contrast increases the proportions of superimposed perception (Brascamp, van Ee, Noest, Jacobs, & van den berg, 2006; Liu et al., 1992) and also to test Levelt's laws of CBR that are describing the relationship between stimulus strength and perception during CBR (Brascamp et al., 2015; Levelt, 1965). A white central spot of 0.1° diameter was used as a fixation marker. A circular fusion lock (width of 2 pixels) surrounded the stimuli with 3° radial distance from the center of the stimuli. Stimuli were presented on a grey background with a mean luminance of 61.9 cd/m2 in a windowless room with constant artificial lighting condition. An alpha blending procedure was used to merge two orthogonal gratings presented within a gaussian window and were updated in real time to joystick movements.

Changes to the physical stimuli were created with bandpass filtered noise that was used to spatially combine the orthogonal gratings. Random gaussian noise was filtered with a log cosine filter whose peak spatial frequency (Fpeak) was varied with joystick movements along the vertical axis. Fpeak varied in log steps from 1 cycle per image at the minimum vertical joystick position (closest to the partici-pant) to the Nyquist limit at the maximum position (farthest from the participant). This created regional blobs whose size varied from half the stimulus size when the joystick was at the near position to 1 pixel when the joystick was at the far central suppression. The Miles eye dominance test was carried out to determine the eye dominance. Here, the participants were asked to fixate the experimenter's right eye through a small gap made by folding their hands. We also asked whether the participant was left or right-handed. Two participants were excluded (one attention-deficit, one epilepsy) from the main analysis. Ten participants wore glasses, three contact lenses, fifteen did not wear spectacle correction.

TABLE 2

Demographic and optometric screening data. Mean age, sex assigned at
birth, handedness, Miles test eye dominance, mean visual acuities
and range [Snellen acuity] for right (OD), left (OS), and both
(OU) eyes, and mean stereoacuity in arc seconds and range are depicted.

| Total # participant n/ included n | Age [years] [Right/Left]* | Sex [f/m] | Handedness [Right/Left]* [20/_] | Eye Visual dominance | Stereoacuity@41 cm acuities@4 m [arcsec] |
|---|---|---|---|---|---|
| 30/28   18.6 [17-34] | 15/13 | 25/2 | 18/9 | OD: 14.5 [10-20] OS: 15.6 [13-20] OU: 14.2 [10-20] | 40 [40-50] |

*Missing information for one participant.

position. The noise was scaled to the range −1 to +1 with zero mean. A cut off value between −1 and +1 was used to assign pixels to either the 135° or 45° grating.

The cut off value was varied in linear steps with joystick movements along the horizontal axis. Areas of the bandpass filtered noise with values below the cutoff (darker noise areas) were assigned to the 135° grating and values above the cutoff (lighter noise areas) were assigned to the 135° grating. Thus, when the joystick was fully to the left, the blended image was a uniform 135° grating; when it was fully to the right, the blended image was a uniform 45° grating; when it was fully near the blended image was 2 large blobs one with a 135° grating, the other with a 45° grating; when it was fully far the blended image was a transparent 135° and 45° grating. A new noise sample was created at the start of each test period.

Dichoptic Grating Stimuli

Polarized glasses (LG Cinema 3D, AG-F310) ensured dichoptic representation of the stimuli via a 3D monitor in which the pixels are. All other properties were the same as for the non-dichoptic grating stimuli.

Participants

All participants except author J.S. were students at the Northeastern University, MA, USA. No participants, except author J.S., had experience in rivalry experiments nor were they aware of the design of the study. Initially 30 participants took part in this study (Table 1). General exclusion criteria from the main analysis were: diagnosis of autism, attention deficit disorder, epilepsy, migraine, dyslexia, or any other mental health condition.

Prior to the experiments, an optometric screening was carried out by an optometrist (author J.S.) to ensure normal binocular vision. Specifically, all participants had normal or corrected-to-normal monocular visual acuities measured in 4 m distance to a retro-luminant ETDRS chart of at least 20/20, a binocular acuity that was the same or higher, and reported that they had no ocular-related surgery or treatment in the past. Normal binocular vision was then indicated by measuring stereoacuity using the Titmus test (stereoacu-ity≤100 arcsec). A Worth 4-Dot test for the distance of 1.5 m was carried out to test for central interocular suppression and all participants perceived 4 lights, indicative for no Psychophysical Procedure After the optometric screening, the participants were broad to the lab in which the joystick experiment was carried out. First the chair, chin and forehead rest were aligned so that the participant was sitting comfortably. The joystick was placed on the right-hand side and was used by all participants with their right hand. Polarized glasses were worn throughout the experiment without further explanations to ensure that participants remained blinded to the task and to keep the contrasts for all phases constant.

As shown in FIG. 3, during phase 1) ("Indicate me"), participants first freely explored the relation between joystick and physical stimulus change in all joystick directions during a training trial, followed by the actual session in which the participant was asked to indicate and explore the space in which each state of the six predefined state that had been reported previously, namely exclusive left and right (e.g. Breese, 1899; Lunghi, Burr, & Morrone, 2011), piece-meal (e.g. Klink, Brascamp, Blake, & van Wezel, 2010; von Helmholtz, 1867), equal superimposition (e.g. Liu et al., 1992; Skerswetat et al., 2018), and perception of superim-position and piecemeal with either left or right predomi-nance (Sheynin, Proulx, & Hess, 2019b) was being per-ceived (i.e. one state at a time, 10 sec/state). For example, the participants were asked to indicate and explore the joystick space for a left exclusive percept which would lead to a left-of-center movement of the joystick. During phase 2) ("Follow me"), the participant was instructed to use the joystick and follow the perceived changes of the stimulus as soon as they were noticed by tilting the joystick into the dedicated directions learned during phase 1) while observing dynamically changing stimuli. Note that the participant was being made aware that this was indeed a physical alternation phase rather than a perceptual rivalry alternation. Each trial was initiated via joystick pull and release of the trigger, lasted 60 secs and were stopped abruptly by the program. To ensure the task was understood, the experimenter observed whether the approximated joystick location and stimulus appearance were aligned, e.g. exclusive left stimulus means joystick left tilted, equal superimposition means joystick tilted forward etc. and verbally explained what movement was expected during the first alternations of the first trial. All participants were able to perform the task. After the last trial, a break was given and followed by phase 3) ("Rivalry") during which the task remained the same as during phase 2) while now perceptual rather than physical changes were being tracked. After completion of that phase and another break, phase 4) ("Replay me") started with the same task as for phase 3).

The initial Phase 1) consisted of two 1 min trials, and then only 1 min trial, phases 2-4) included eight trials/phase. Three contrast conditions were used, namely 0.1 vs 0.1, 0.5 vs 0.5, and 0.1 vs 0.5 counterbalanced between the eyes. Stimulus orientations were also counterbalanced between trials. Each contrast was used for all 4 phases of InFoRM: Rivalry, the order of contrasts was randomized between participants. The completion of the entire experiment, include the screening, took approximately 120 min.

Data Analysis

Raw data consisted of in total 3600 data point for horizontal and vertical joystick vectors for each phase and was stored in customized .mat files.

Data Processing During the Experiment

Phase 1) "Indicate Me"

The horizontal and vertical joystick data for each of the six perceptual states lasted sec/600 data points and were stored in a .mat file and used as ground truth for phase 2).

Phase 2) "Follow Me"

Inventor J.S. generated actual binocular rivalry joystick data for 60 sec/3600 data points for varying contrast conditions and stored them as training data. Phase 2) consisted of 4 trials of those mimic data and 4 trials made of the individuals Phase 1) data, each state's input randomly connected within a trial. All mimic and Phase 1) trials were then randomized. The participant had thus the opportunity to train t follow an actual rivalry experience as well as had to indicate each of the six states, generate by the participant themselves.

Phase 3) "Rivalry"

Eight trials, each consisting of 60 sec/3600 data points were collected per contrast condition and stored as .mat file.

Phase 4) "Replay Me"

Data from Phase 3) were read in and used to generate physical stimulus changes during phase 4). The eight trials of joystick data were then again stored as separate .mat file.

Post-Experiment Data Analysis

A customized Matlab (Version 2021a) program was written to analyze the raw data.

Classification of Perceptual States Generated During Phase 2) "Follow Me"

Using the joystick indications during the phase in which the each of the six principal states were shown, generate by each individual during the "Indicate me" phase. Each state consisted of 600 data points. A Gaussian Mixture model was used to determine the most likely location for each perceptual state Phase 3) "Rivalry" Data Analysis The joystick data generated during phase 3) and the classification data as described above were used to calculate traditional measures of binocular rivalry. InFoRM: rivalry also to generate recently described measures such as HMMs and novel approaches such as rivalry-speed subtypes e.g. "rivalry-saccades" and "rivalry-tremors" borrowing analysis strategies from eye tracking research.

Relative Proportions, Mean Durations, Perceptual Alternation Rates

A single data point represents 16.7 ms duration. The classification data were used and assigned each phase 3) "Rivalry" data point to each state, which allowed calculation of the mean duration of each state and the relative proportions per trial. Those results were averaged across trials for each participant. Also, changes of classified states were counted for each theoretically possible alternation type, e.g. exclusive left to piecemeal, piecemeal to exclusive left etc. for each trial and then averaged across trials for each condition. Next to the breakdown of all single alternation types, we generated three alternation categories: all flips, i.e. total sum of all occurring alternations, exclusive to mixed states alternations, vice versa, i.e. sum of flips between exclusive and mixed states, and mixed to mixed alternation, i.e. the sum of all within mixed perceptual alternations. The contrasts during the low vs high condition were counterbalanced and we arranged the data for post-processing accordingly.

Analysis of Perceptual Phase Distributions

For each trial, contrast condition, and participant, data was first normalized by dividing the phase durations by the relevant mean. These normalized data were then combined across participants and contrast conditions. The perceptual phases are presented in the following form using a gamma distribution:

$$f(x|\alpha, \beta) = \frac{1}{\beta^\alpha \Gamma(\alpha)} x^{\alpha-1} e^{\frac{-x}{\beta}} ; x > 0, \alpha > 0, \beta \geq 0$$

The gamma function is indicated with $\Gamma(\alpha)$, the "shape" parameter is $\alpha$ and represents the skewness of the distribution, the "scale" parameter $\beta$ scales the distribution along the abscissa and the number of perceptual events $\chi$ (Levelt, 1965; Veser et al., 2008; O'Shea et al., 2009). The coefficient of determination ($R^2$) has been used in previous studies (Logothetis, Leopold and Sheinberg, 1996; O'Shea et al., 2009; Sutoyo and Srinivasan, 2009) as an indicator of how well actual data fit a predicted model; the closer $R^2$ is to 1, the better fit of the model to the actual data. Also, we analyzed the area under the curve (AUC) of the Gamma function, calculated the peak of each function, latency (X-peak), and its amplitude (Y-peak). To be comparable with previously reported data, the range of the x axis went from 180 ms to 4000 ms.

Eye Dominance Score

A general eye-dominance score, i.e. percentage of time spend in left-vs. right-of-joystick-center for each trial, was determined and averaged those across trial, participants, and conditions. This score may be helpful for clinical assessment of overall eye dominance in conjunction with the relative values for each state.

Perceptual Velocity: Rivalry "Fixations", "Tremors", "Micro-Saccades", "Saccades"

Joystick movements are captured by 3600 data of horizontal and vertical locations that may change across trial duration, depending upon the perception was stable (i.e. no joystick movement) or perception alternated (i.e. joystick was tilted). Here, we apply eye tracking techniques used to classify different eye movement subtypes. First, we calculated for mean velocity and its standard deviation (SD) for each trial, then created the following four categories: 'Stable perception' (Speed=0), 'Rivalry tremor' (Speed>0 & <mean), 'Rivalry Micro-saccades' (Speed>=mean & <=1 SD), and "Rivalry Saccades' (Speed>SD). Then we averaged those speed categories across trials and contrast conditions, used a one-way Analysis-Of-Variance (ANOVA), Within Mixed State Analysis To explore the changes within each of the four mixed states, we deployed first the speed analysis technique for each perceptual state. Specifically, we first identified whether within each trial piecemeal, equal superimposition, or left and right predominance superimposition occurred. If so, the perceptual velocity method described above was deployed for each subtype within each mixed state.

Furthermore, the of blob size of each stimulus input during phase 3) was estimated within the mixed phases and their distribution and mean size analyzed.

Results

Due to the large amount of data and techniques applied, only averages across conditions are reported.

Follow-Me Classification

Perceptual state sizes varied within and between contrast conditions as indicated in FIGS. 6A-6I.

Standard Rivalry Measures

Figure 5A:
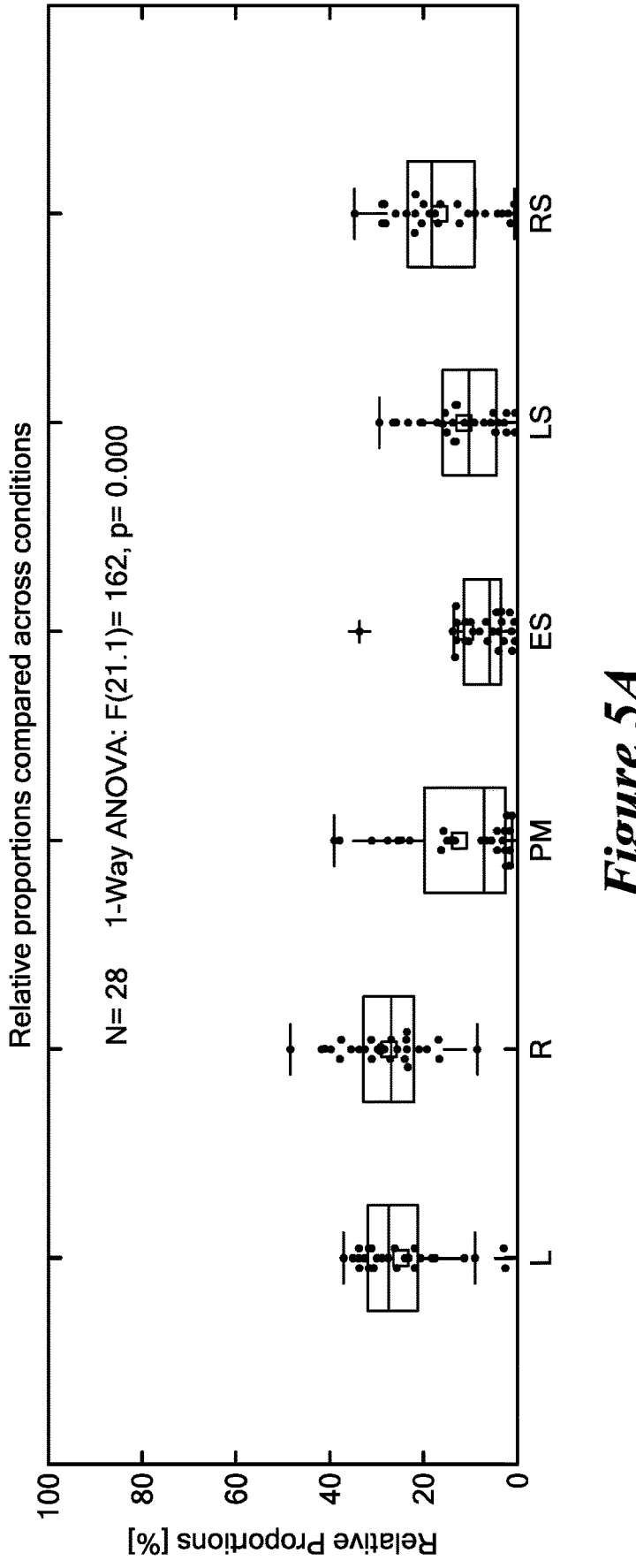
FIGS. 5A-5D show results for standard measures generated by InFoRM Rivalry. Averages across trials, participants, and conditions for relative proportions (5A), mean durations (5B), sum of all perceptual flips (5C), and Gamma function fits to normalized exclusive percepts with their respective histograms (5D) are depicted. 'L,' 'R,' 'PM,' 'ES,' and 'RS' in 5A-5C refer to sum of left and right exclusivity, piecemeal, equal superimposition, superimposition with left predominance, and superimposition with right predominance, respectively and 'All,' 'rEVtoMixed,' and 'MixedtoMixed' in 5C to all flips, flips from exclusive to any non-exclusive state, and flips within mixed states, respectively. The scattered dots indicate data for each individual, squares depict the means, boxes the interquartile ranges (25th-75th percentiles), horizontal lines within each box the medians, whiskers extend to the extreme values, outliers are plotted outside the whiskers. One-way ANOVAs were performed to test for difference between states or alternation categories.
Figure 5B:
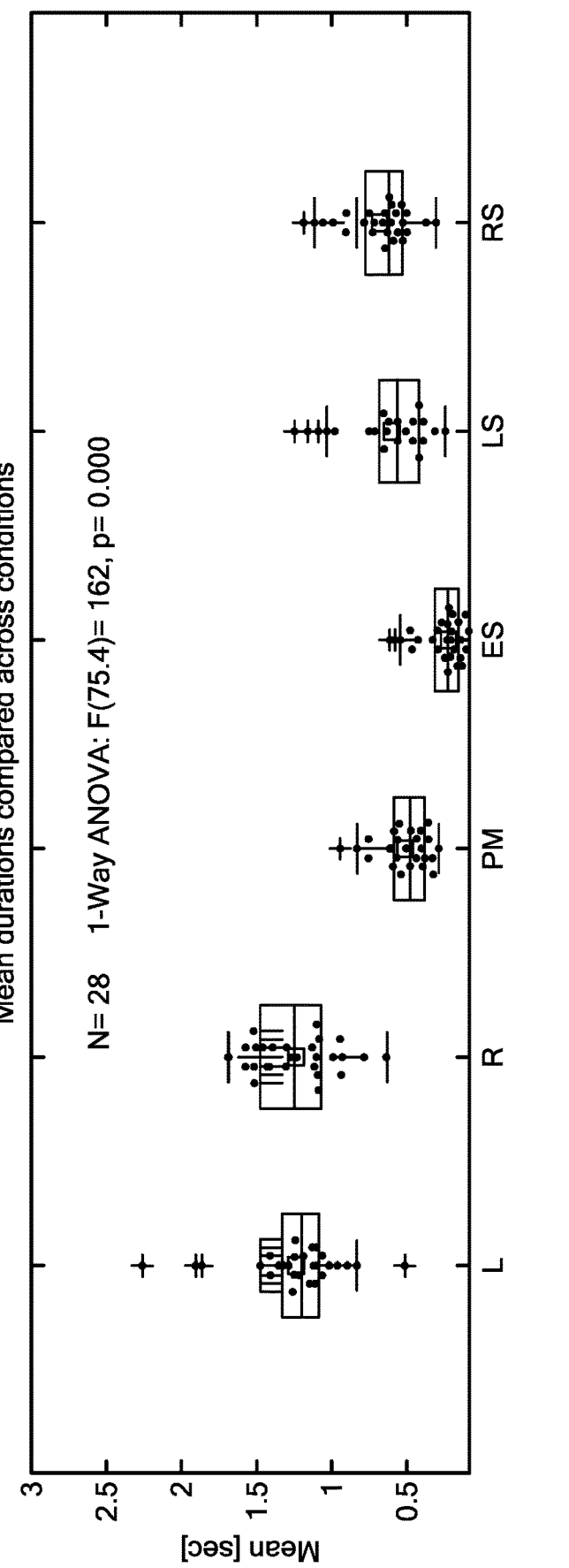
Figure 5C:
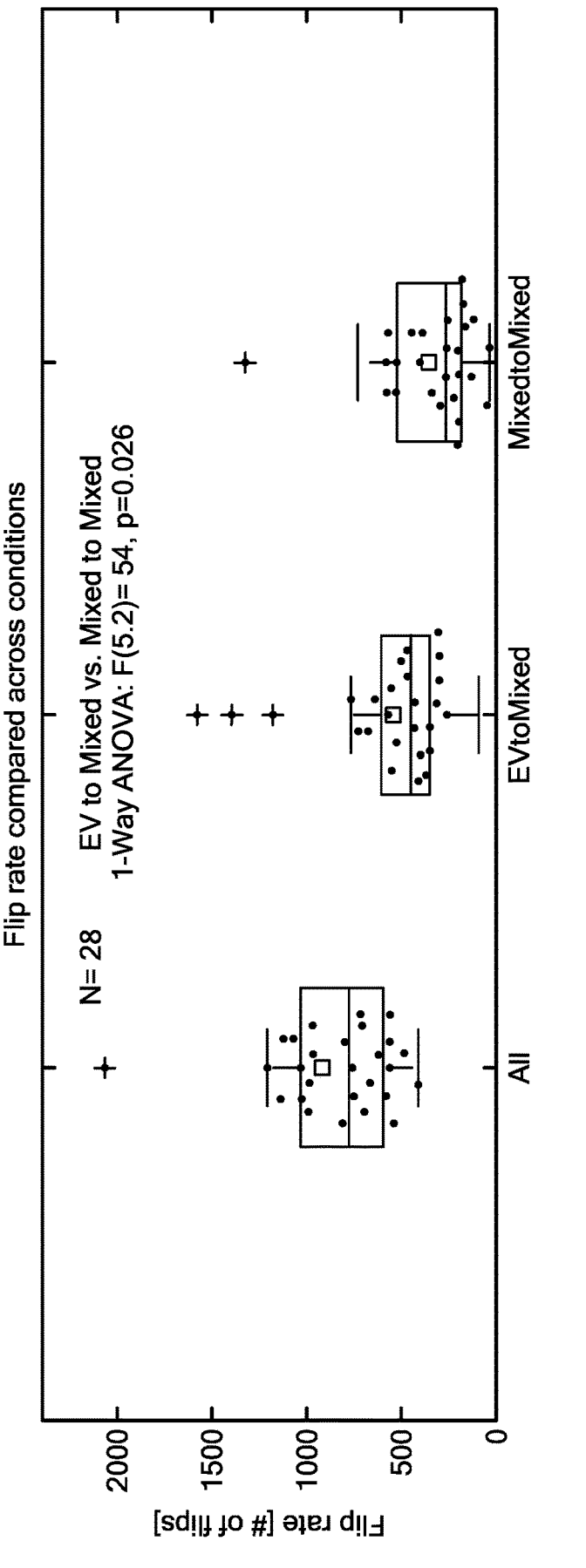
Figure 5D:
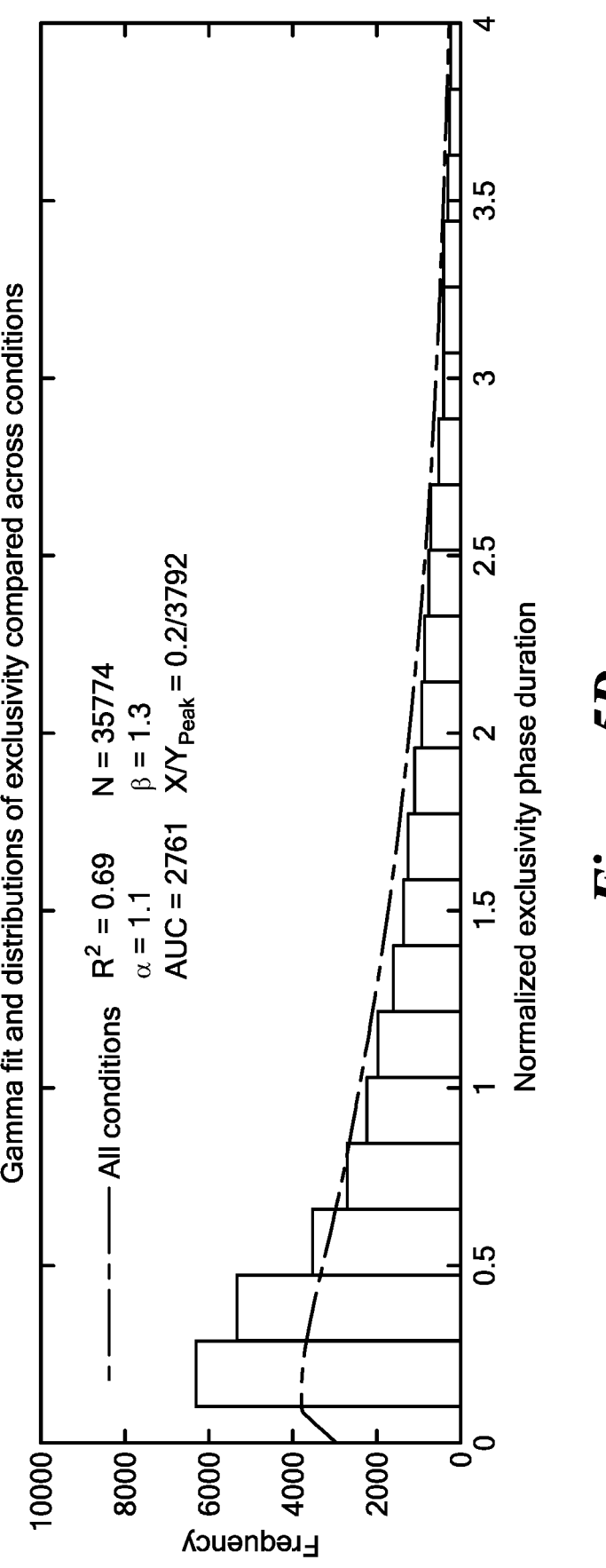
Figure 6A:
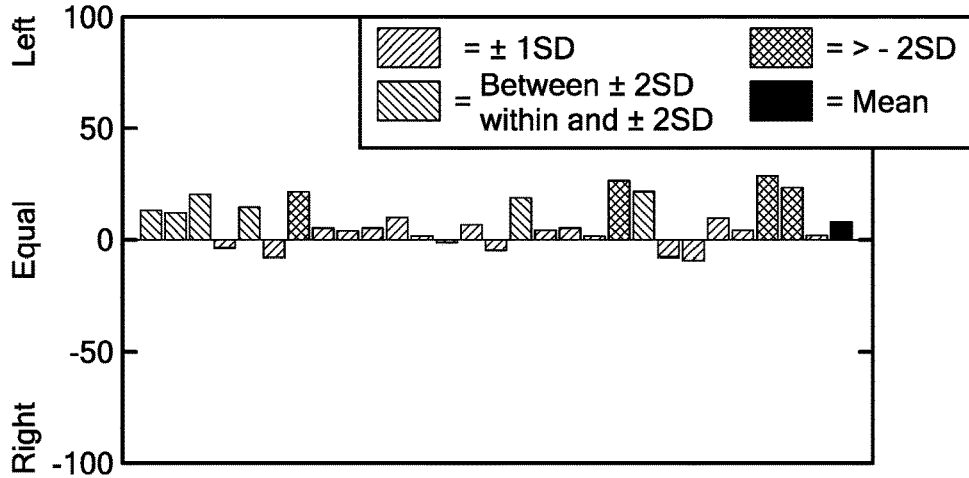
FIGS. 6A-6I show eye dominance scores for Low (6A-6C), High (6D-6F), and Low vs High (6G-6I) contrast condition. Individual differences between left minus right eye's values (6A-6F) or Low minus High contrast (6G-6I) are shown either within ±1SD (green), between ±1SD within and ±2SD (orange), and ±2SD (red). Black bars on the right of each graph depict the mean across participants within condition.
Figure 6B:
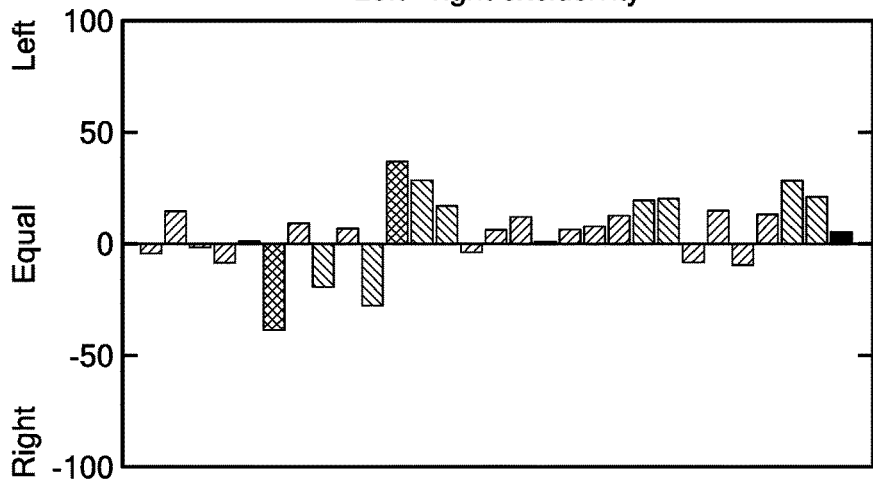
Figure 6C:
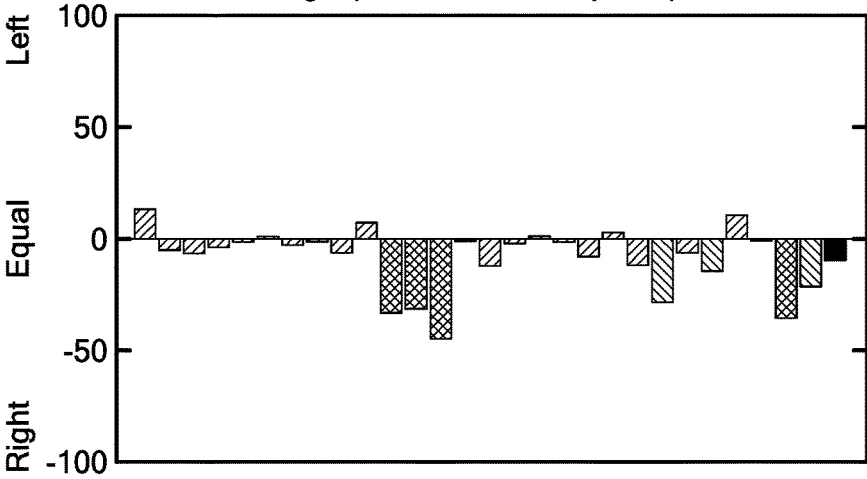
Figure 6D:
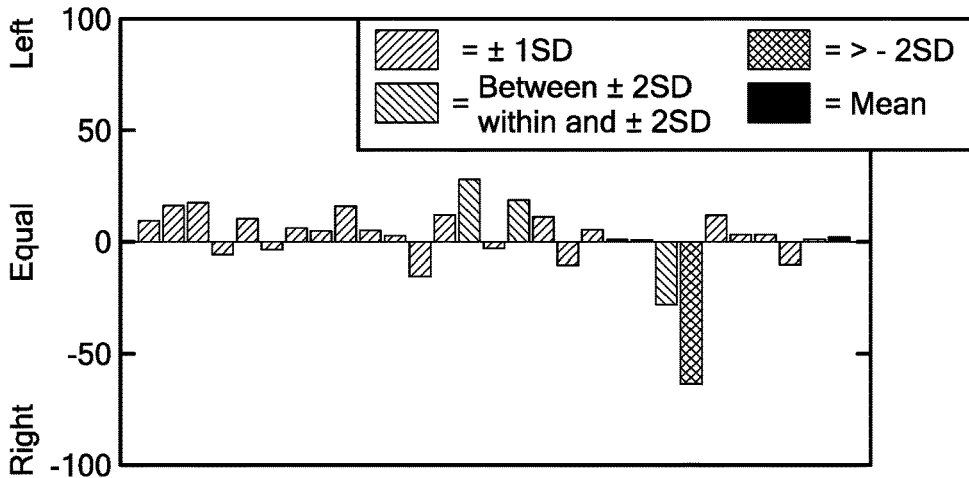
Figure 6E:
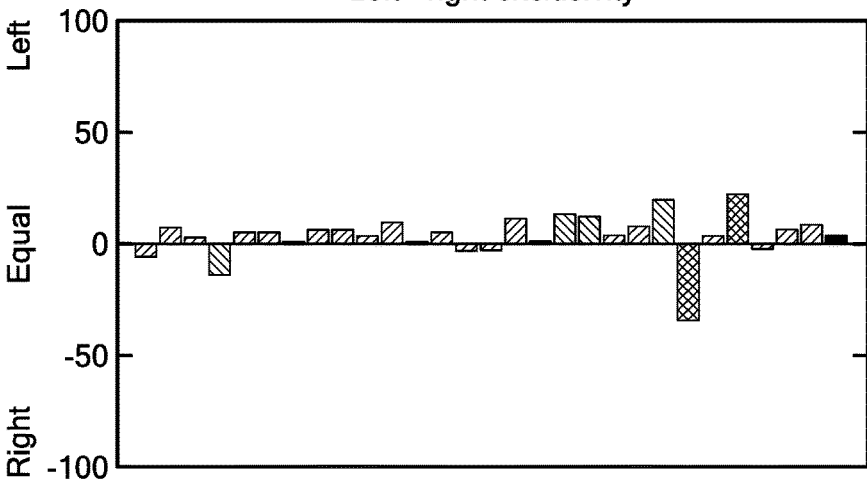
Figure 6F:
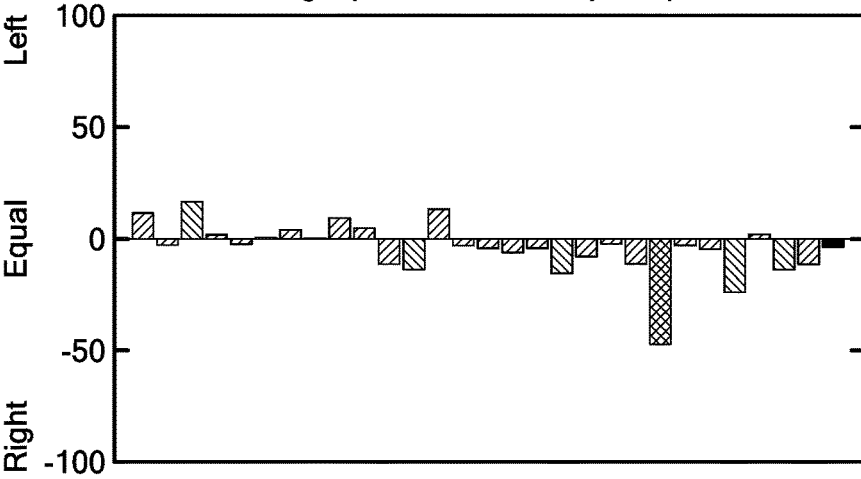
Figure 6G:
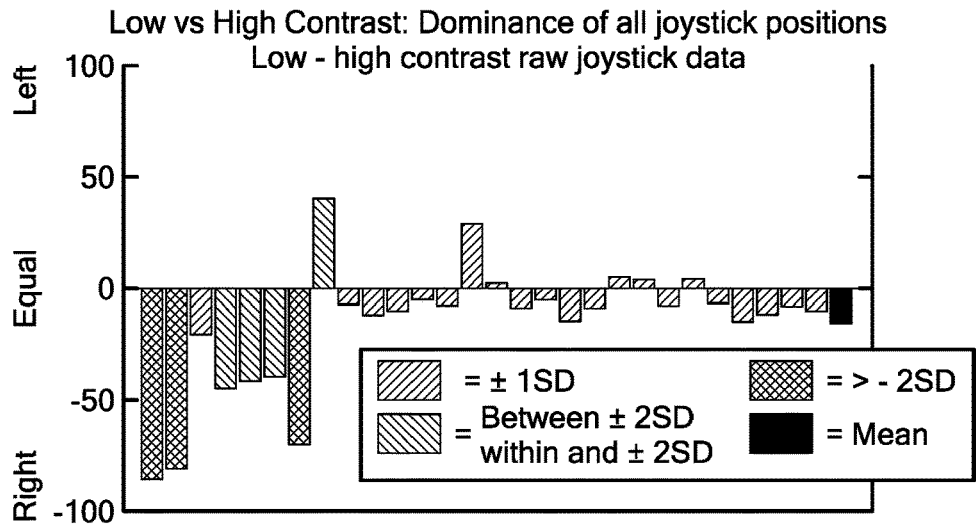
Figure 6H:
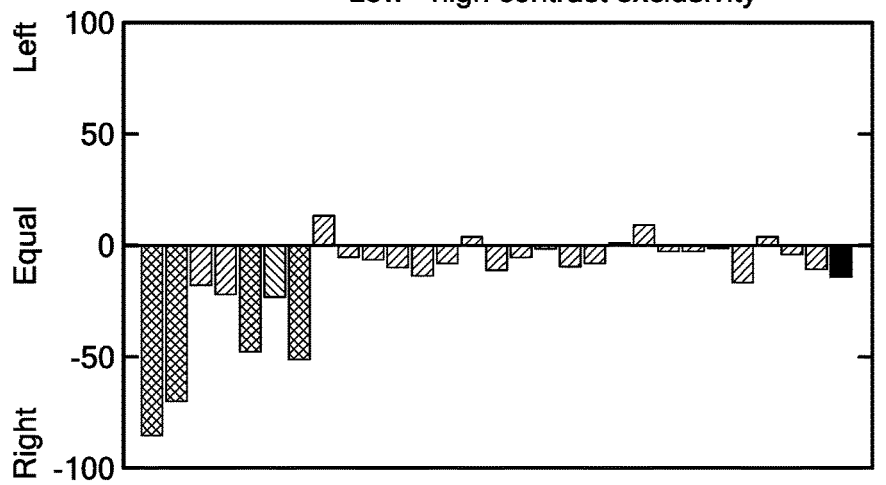
Figure 6I:
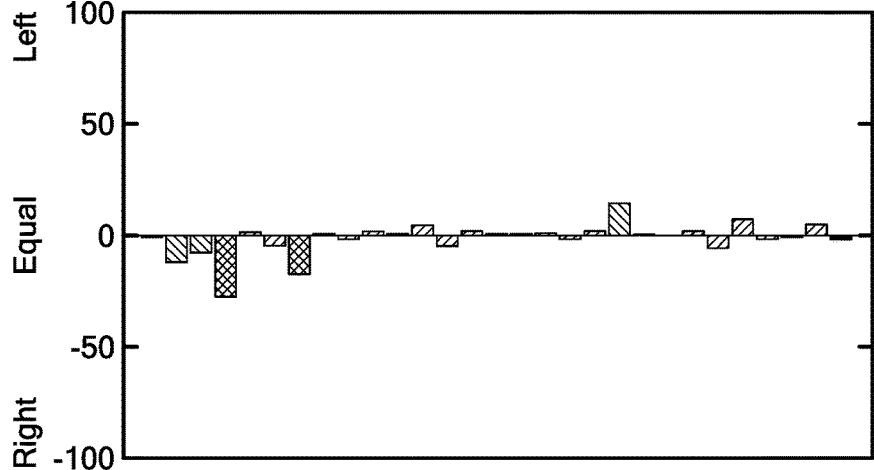
Figure 7A:
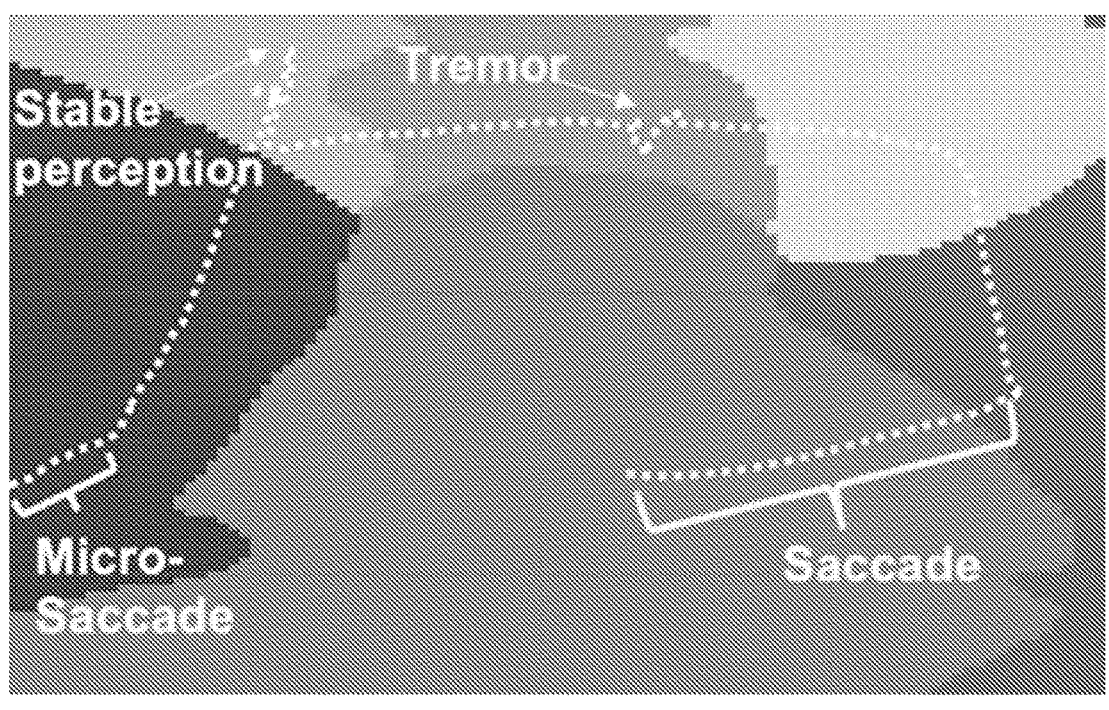
FIGS. 7A-7F show analysis of perceptual velocity during binocular rivalry.
Figure 7B:
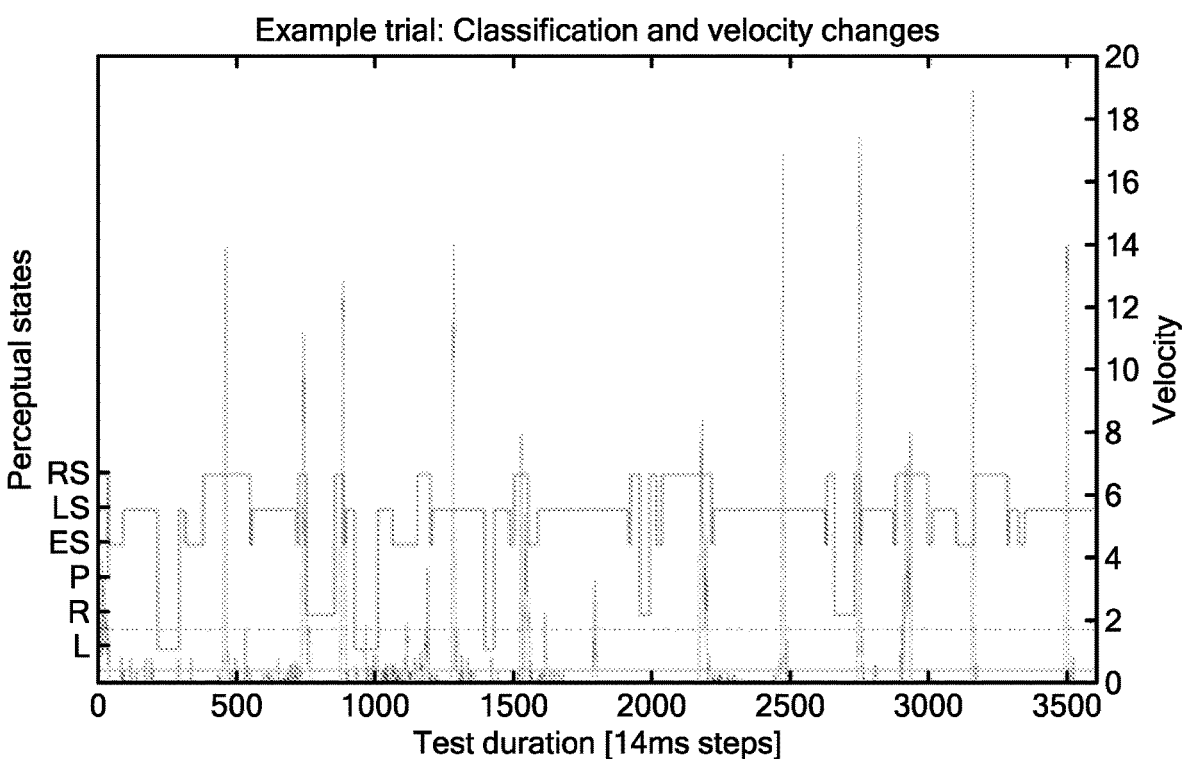
Figure 7C:
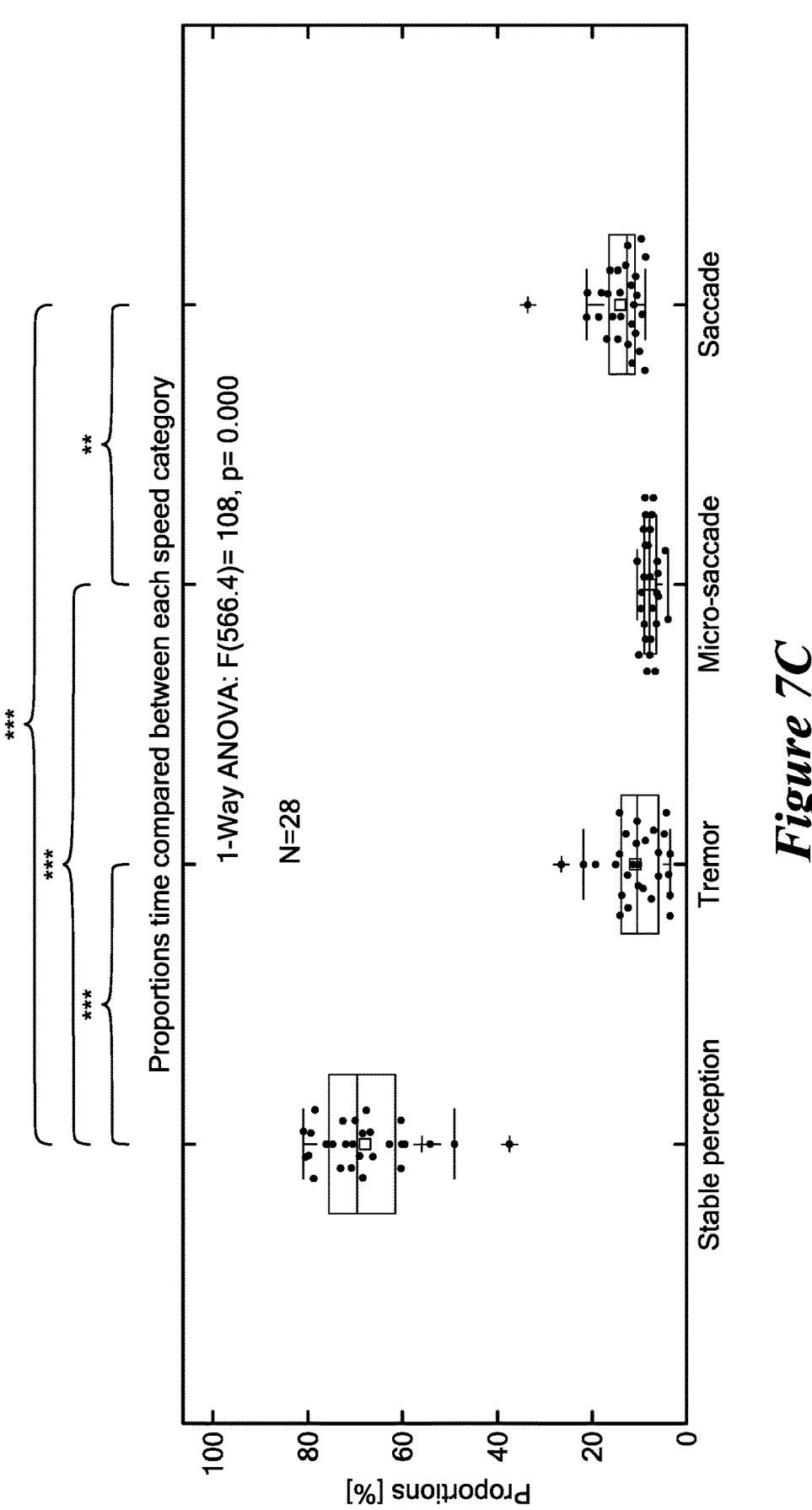
Figure 7D:
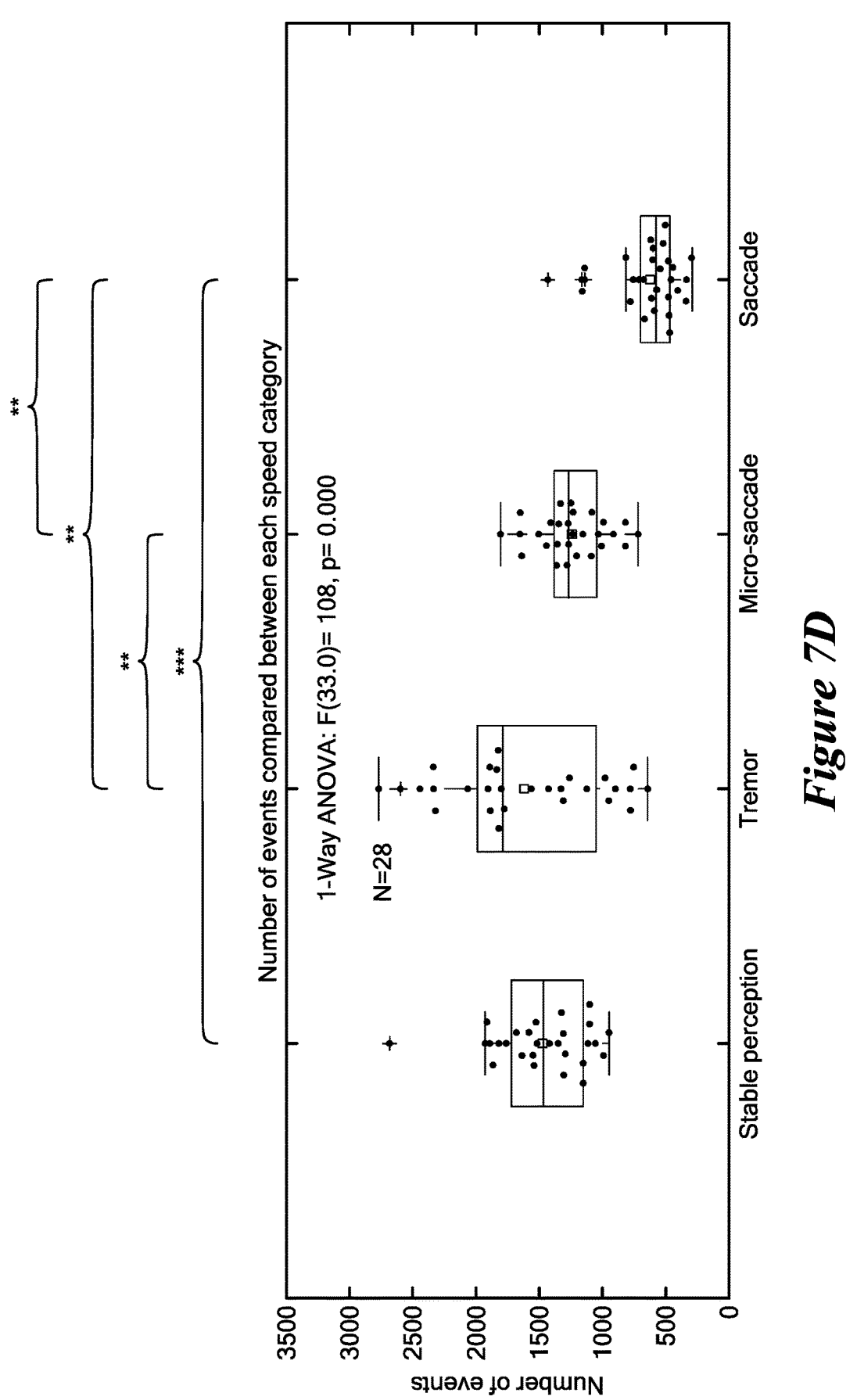
Figure 7E:
Figure 7F:
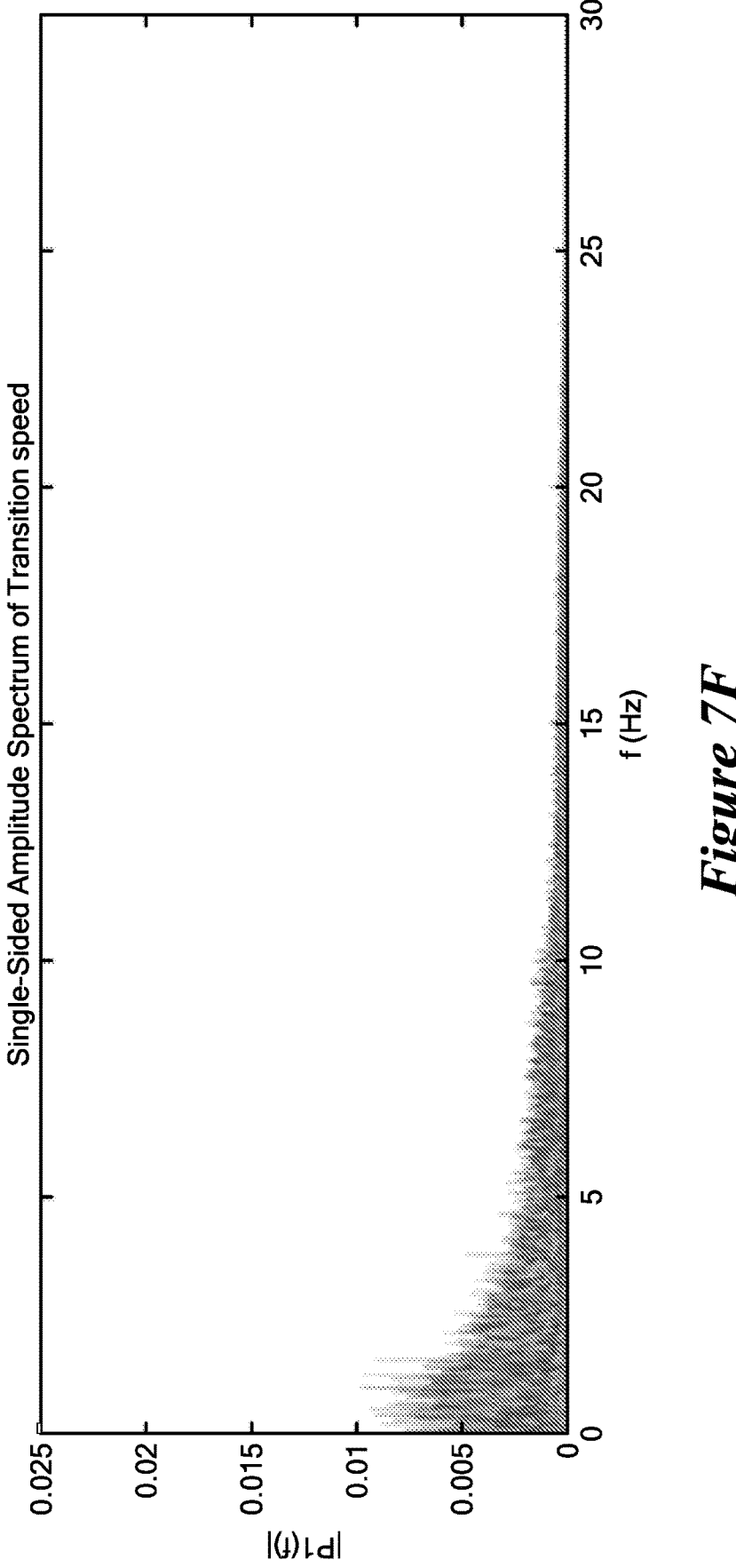
Figure 8A:
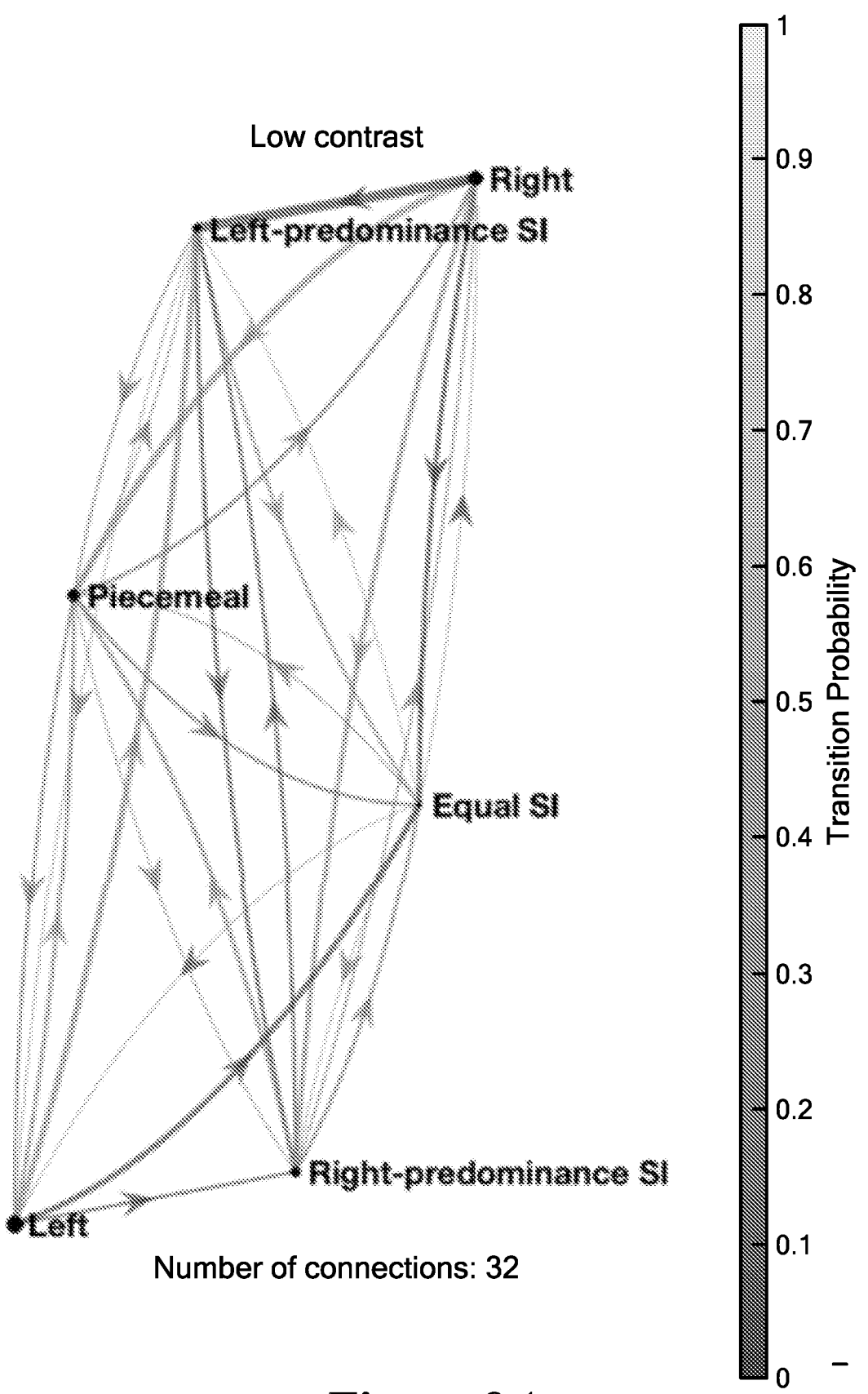
FIGS. 8A-8C show Markov chains indicating likelihood of each state.
Figure 8B:
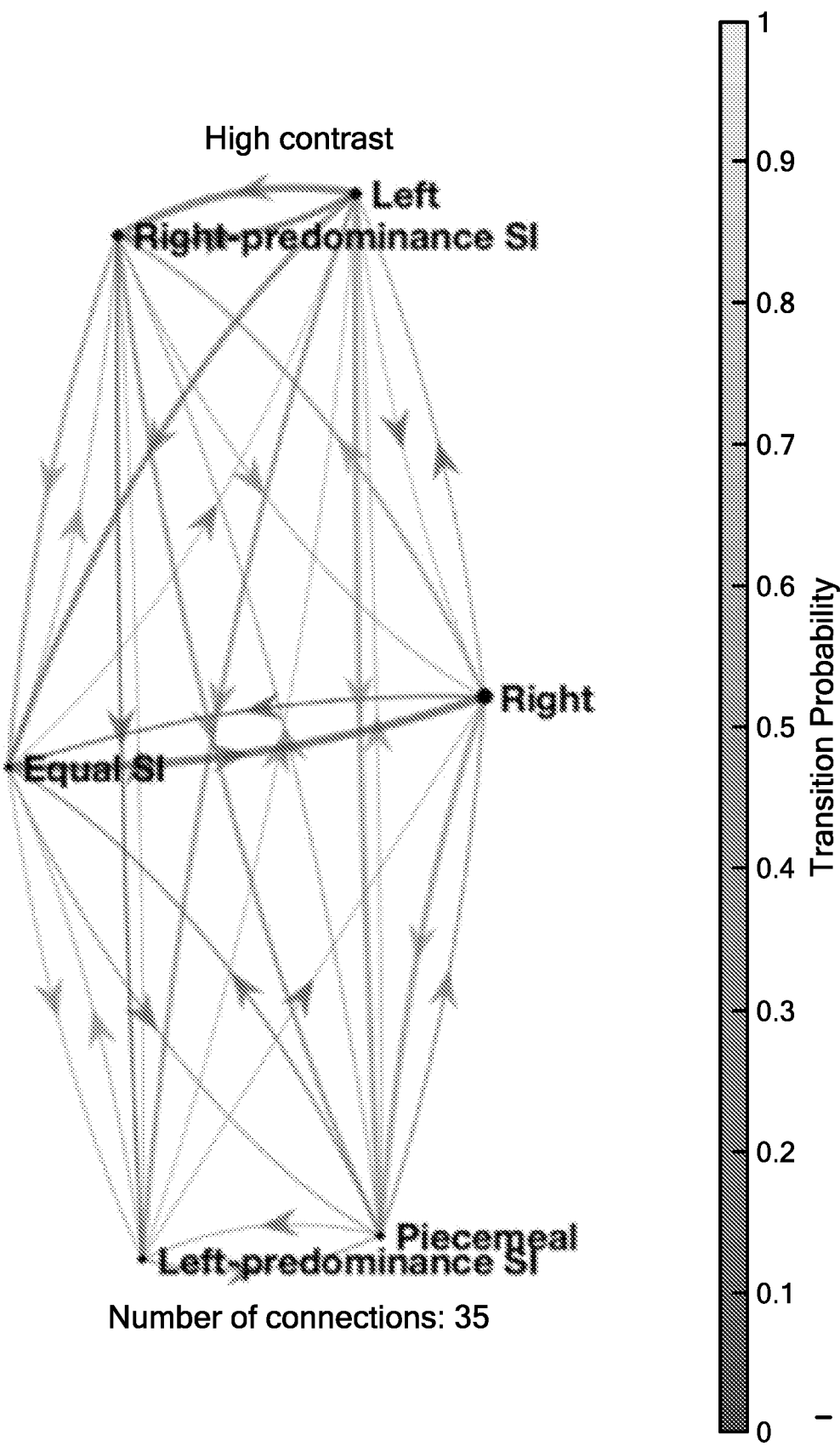
Figure 8C:
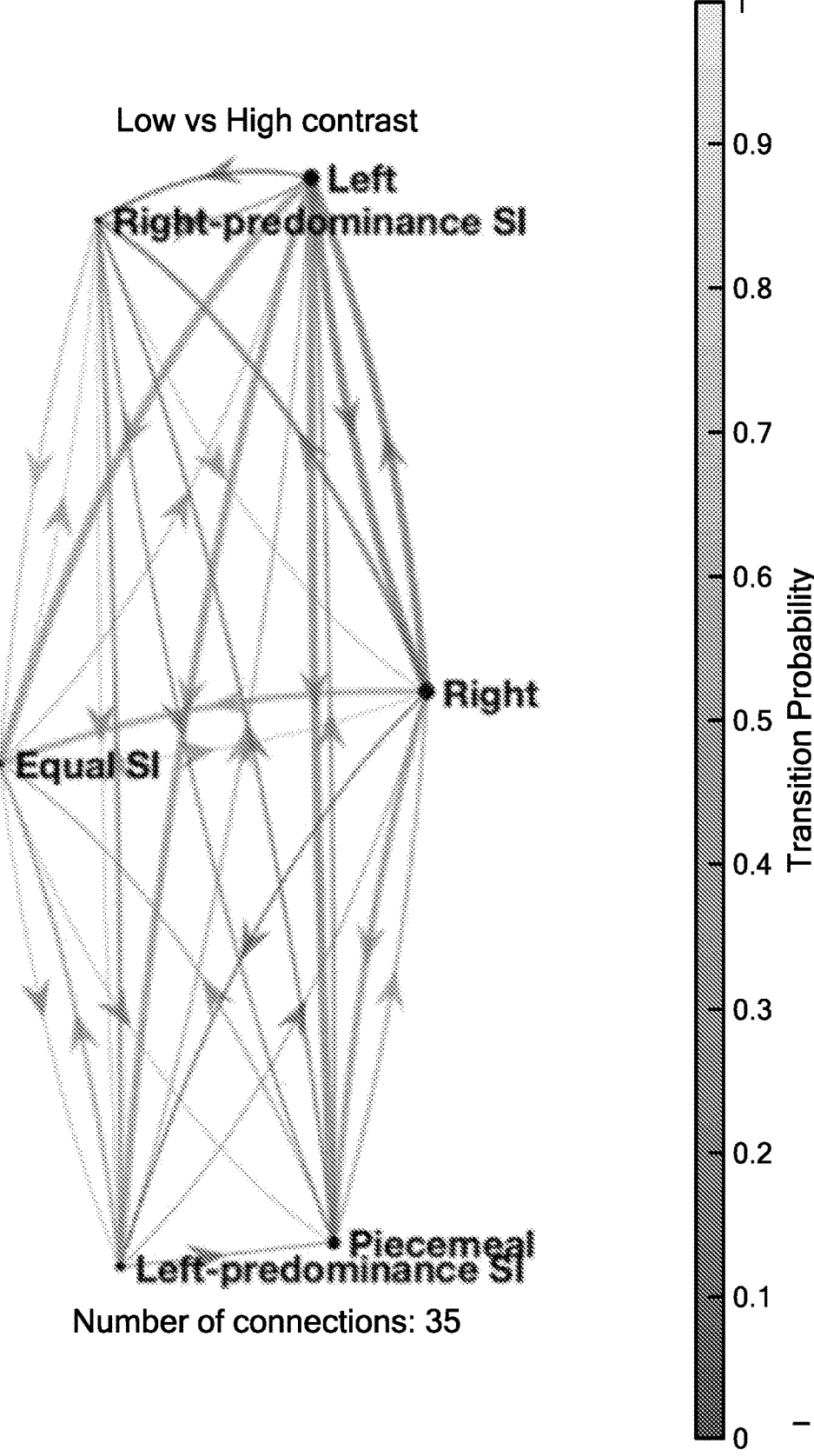
Figure 9:
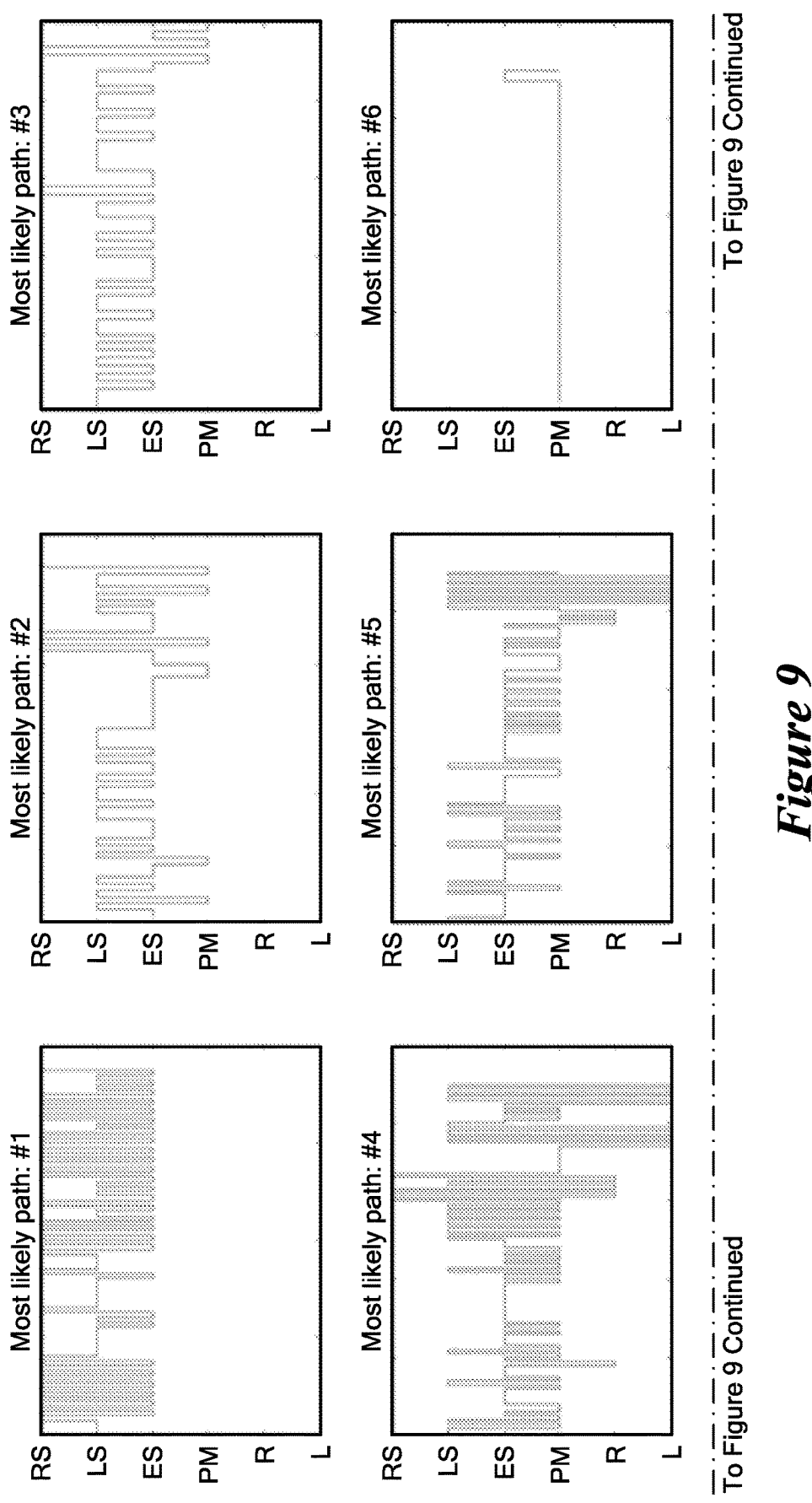
FIG. 9 shows Hidden Markov Model predictions of the most likely perceptual path for each subject during low contrast conditions.
Figure 9:
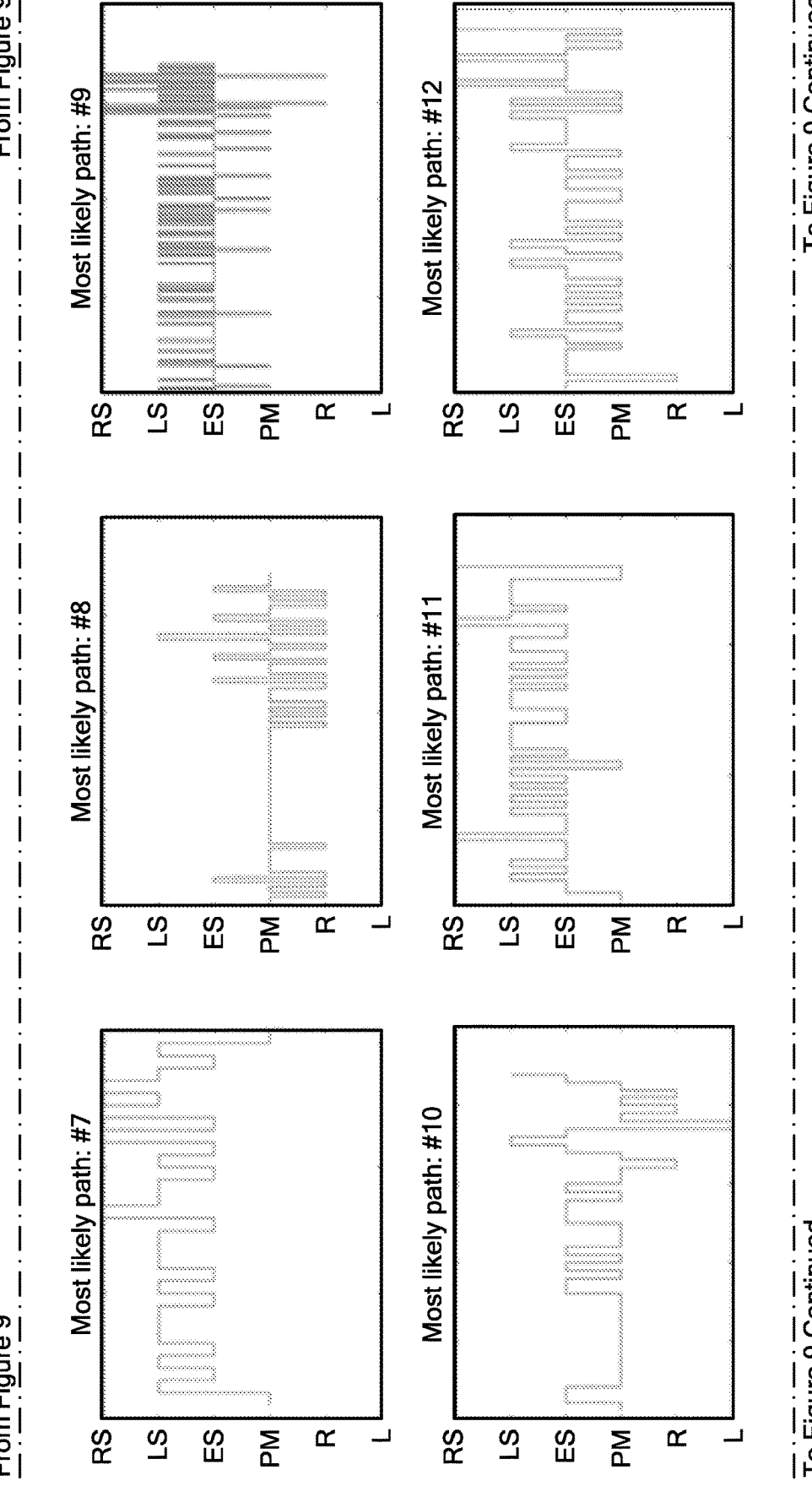
Figure 9:
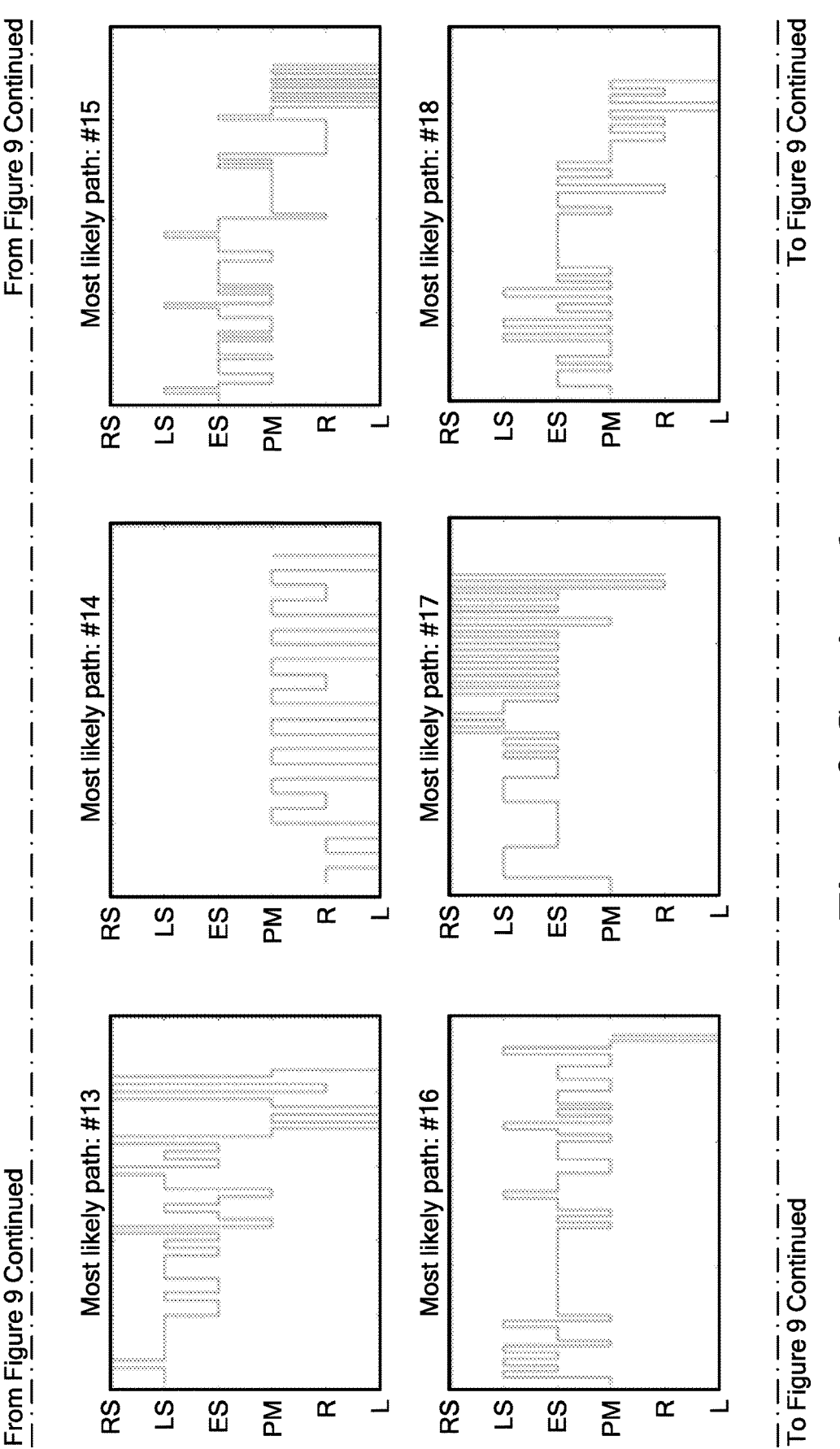
Figure 9:
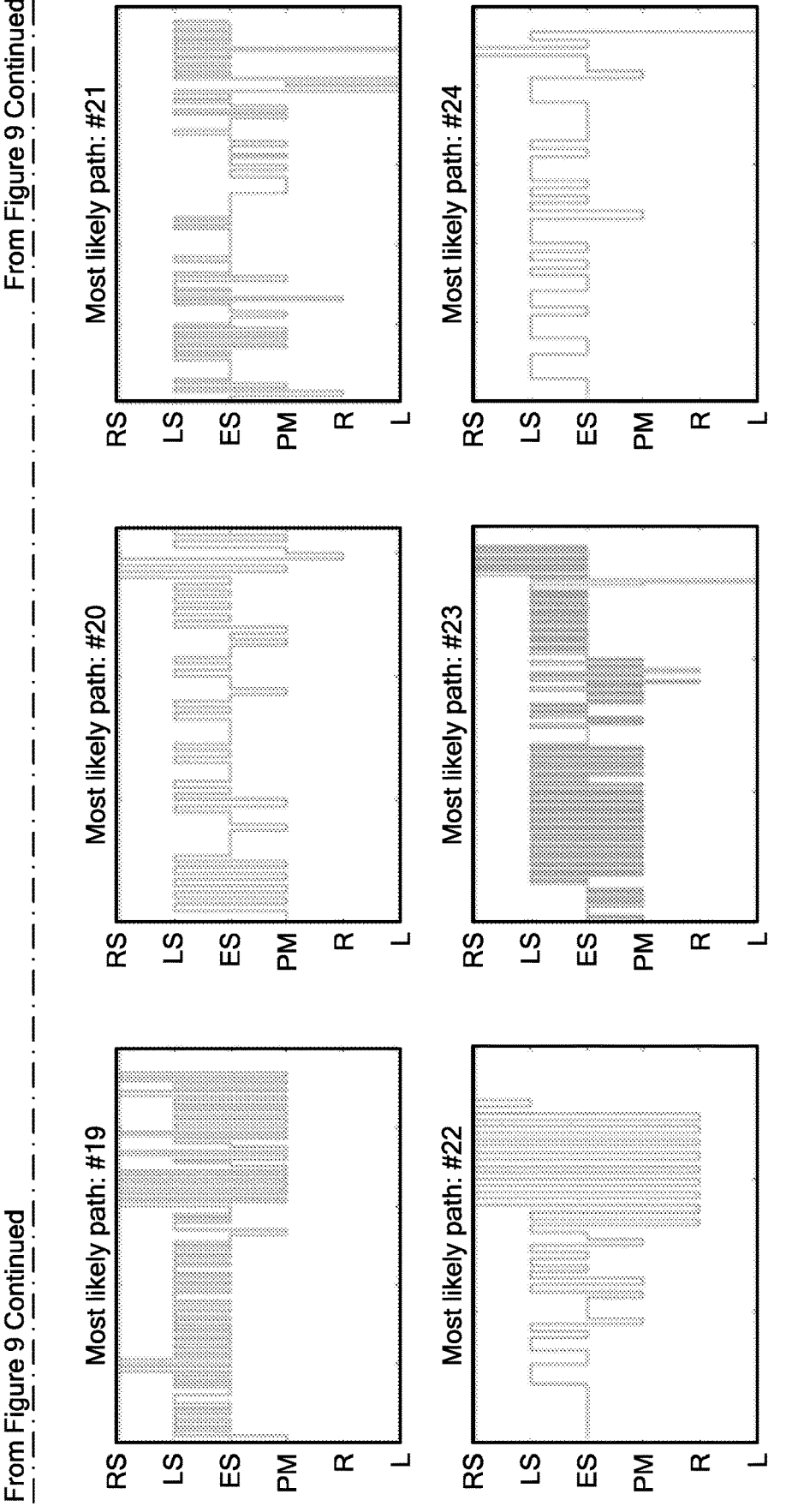
Figure 9:
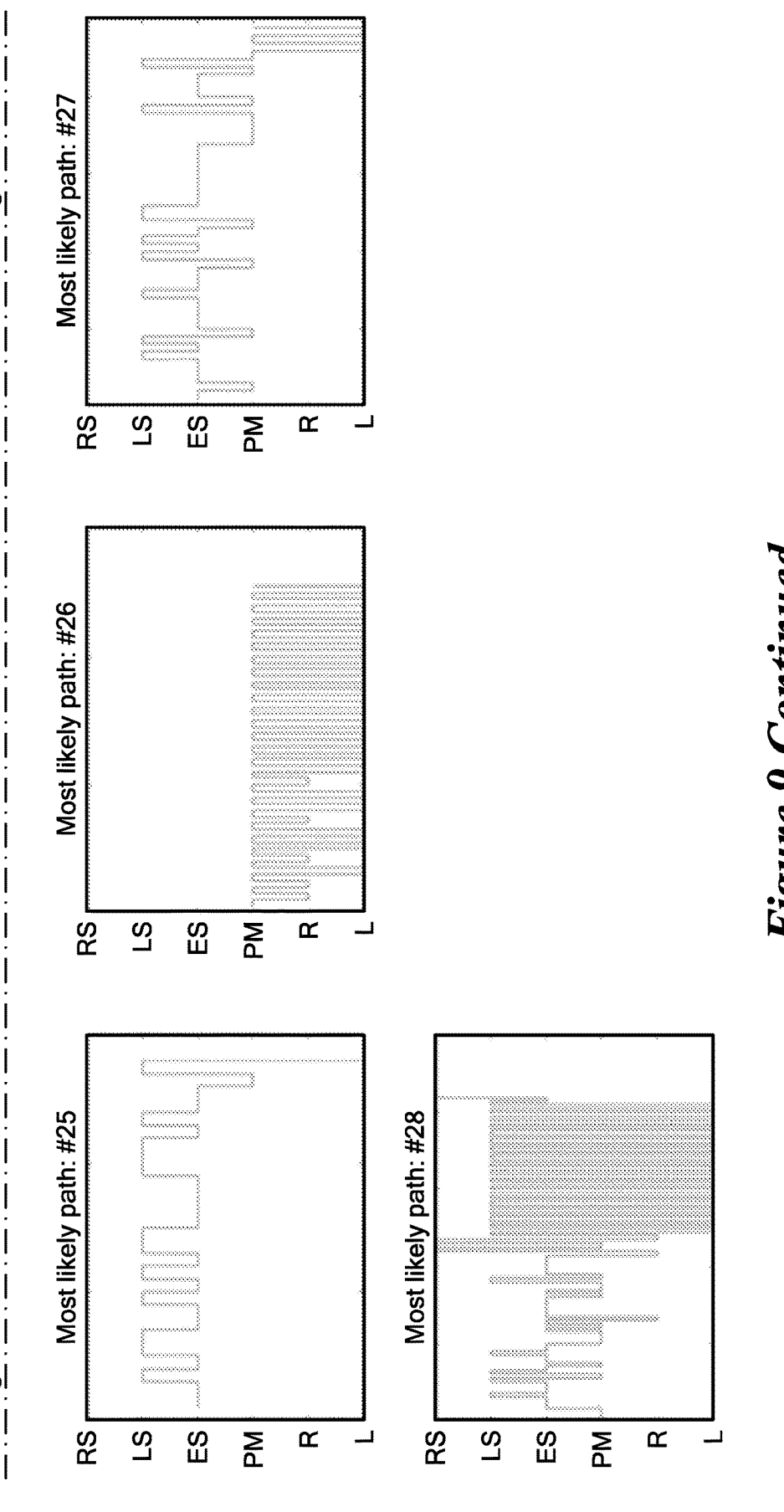

InFoRM Rivalry is to our knowledge the first paradigm that continuously measures six perceptual states within a trial. A significant effect of perceptual bias was found (see FIG. 6A) due to greater portions of left and right exclusivity compared to the other states. Previous studies using comparable stimulus configurations that reported portions of exclusive versus mixed perceptual states showed that mixed or exclusivity are being perceived approximately 50% of the test duration (Hollins, 1980; Skerswetat, Formankiewicz, & Waugh, 2016), which is in line with the results gained with InFoRM: Rivalry (52%±9 (Standard deviation (SD)) exclusivity and 48%±9 mixed perception). Moreover, we show that piecemeal 12%±12 occurred less frequent than the sum of all superimposed states 35%±19 (FIG. 5A). The results of the relative portions is accompanied with a significant effect for mean durations (see FIG. 5B). The mean exclusivity durations were with 1.2 sec±0.3 longer than the mean mixed duration (0.5 sec±0.2). On average, more perceptual alternation between exclusive and mixed states occurred than within mixed alternations (see FIG. 5C). The distributions of exclusive events during binocular rivalry have been previously shown to be well fitted with a Gamma-function (Levelt, 1965; Zhou et al., 2004), which we replicated using the InFoRM: Rivalry (FIG. 5D) indicated with $R^2$ of 0.69.

The inventors further investigated each possible single flip type in a separated heatmap table that provides a complete breakdown of all types and found that reversions of alternations, i.e. a change from one state to another and back to the previous state does in fact almost never occur (supplementary materials).

Individual data are reported here for each contrast condition to demonstrate that InFoRM detects predominance biases during binocular rivalry, which have been used as tool for determining eye dominance in various clinical populations (Bossi, Hamm, Dahlmann-Noor, & Dakin, 2018). The inventors analyzed the total portions of joystick movement that were either to the left or right of the joystick center as an eye dominance measure. The inventors also used the relative proportions of exclusivity and predominance during superimposition to further investigate sensory eye dominance between these perceptual states. As shown, low and high contrast conditions had overall a left bias (FIGS. 6A and 6D), presumably due to the use of the right hand which makes the leftward movement more natural. The low vs high condition (FIG. 6G) show for most individuals the bias toward the high contrast stimulus, as predicted by Levelt's first and second law of rivalry (Brascamp et al., 2015; Levelt, 1965). These measures may be useful for screening and monitoring of populations with disrupted sensory Perceptual Velocity: Rivalry "Fixations", "Tremors", "Micro-Saccades", "Saccades"

Across trials, conditions, and participants, medians of relative proportions for stable experiences, rivalry-tremors, -micro saccades, and -saccades were 71.2, 9.7, 7.9, 12.1%±2.0, 1.2, 0.4, 1.0 standard errors, respectively. Gamma fits for each FFT across trials, conditions, and participants showed a median scale of 0.8 Hz and $R^2$ of 0.29.

What is claimed is:

1. A method of testing a visual function comprising conscious visual perception, the method comprising the steps of:

(a) providing a test system for presenting a series of images to a subject and receiving physical responses from the subject, the system comprising a stereoscopic or non-stereoscopic viewing device, an input device for continuous physical input in response to physical changes of a displayed image or a perceptual change of unaltered physical images by the subject, a data storage device operative to receive and store data from the input device, and an analysis device configured to analyze the stored data;

(b) displaying to the subject a series of images using the viewing device, wherein the images present a pair of individual images simultaneously to each eye or a multi-stable non-stereoscopic image, in response to use of the input device by the subject, so as to train the subject to actively input perceptual states induced by the displayed images using the input device;

(c) displaying to the subject using the viewing device a series of physically changing images, wherein the images present a simulated combination of a pair of individual images, while the subject actively uses the input device to report said perceptual states continuously, and while data from the input device are stored in the data storage device;

(d) presenting to the subject dichoptically a series of binocular images using the stereoscopic viewing device while the subject actively uses the input device to report said perceptual states, and while data from the input device are stored in the data storage device; and (e) analyzing visual functions of the subject using data reported by the subject in (c) and (d) using the analysis device.

2. The method of claim 1, wherein the method further comprises:

(f) presenting to the subject non-dichoptically a series of binocular images using the stereoscopic viewing device, wherein the series of binocular images simulate dynamically the perceived aspects reported by the subject in (d), while the subject uses the input device to again report said perceptual states induced by dynamically changing, physical images based on the subject's responses in (d), and while data from the input device are stored in the data storage device; and (g) analyzing the agreement between subject's responses in (d) and (f) using the analysis device, wherein said differences provide a measure of test-retest variability of the subject.

3. The method of claim 1, wherein the series of images comprise lines, curves, grating patterns, geometric patterns, faces, or objects, which can be presented statically or in motion.

4. The method of claim 1, wherein a stereoscopic viewing device is used, and the stereoscopic viewing device comprises a head-mounted projection display, a 3D display system, a computer screen, or a display screen of a mobile device or tablet.

5. The method of claim 1, wherein the input device is a joystick, virtual reality flight stick, hand tracker, trackball, computer mouse, touchpad, or touch-sensitive screen.

6. The method of claim 1, wherein the input device provides a series of XY coordinates representative of user input as a function of time.

7. The method of claim 1, wherein the subject is unaware of a transition from step (c) to step (d).

8. The methods of claim 1, wherein the analyzing of step (d) comprises estimation of most likely boundaries of said perceptual states using a Gaussian mixture model, k-means cluster analysis, a support vector machine (SVM), or other machine learning approach to classify said perceptual states.

9. The methods of claim 1, wherein the analyzing of step (e) comprises creation of maps of introspection, and comparison of sizes of the maps corresponding to said perceptual states within and between subject as a validated measure for introspection.

10. The methods of claim 1, wherein the analyzing of step (e) comprises evaluating the mean and relative proportions of each perceptual state, the rate of perceptual state changes, the eye dominance scores in total and for each perceptual state, weighted transition probabilities using machine learning, such as a Hidden-Markov Model algorithm, analyzing the subtypes of joystick changes and thus perceptual changes evaluating the perceptual velocity across perceptual states and within mixed states, and perceptual states related to neuro-receptive field interactions.

11. The method of claim 1, wherein said visual function comprising conscious visual perception is a form of rivalry selected from the group consisting of classic binocular rivalry, interocular grouping, flicker-swap rivalry, continuous flash suppression, and travelling-wave rivalry.

12. The method of claim 11, wherein the visual function is classic binocular rivalry, and the static or moving rivaling binocular images presented in step (d) comprise pairs of images, one for display to a left eye and the other for display to a right eye, and wherein the images of the pair are distinguishable by the subject as exclusively left eye perceptual states, exclusively right eye perceptual states, piecemeal perception as combination of the left and right eye perceptual states, equal superimposition perception of left and right eye perceptual states, left-predominant superimposition perception of left and right eye perceptual states, or right-predominant superimposition perception of left and right eye perceptual states.

13. The method of claim 12, wherein the non-rivaling binocular images presented to the subject in steps (b) and (c) simulate the rivalry depicted in step (d) by being distinguishable by the subject as representing exclusively left eye perceptual states, exclusively right eye perceptual states, piecemeal combination of the left and right eye perceptual states, equal superimposition of left and right eye perceptual states, left-predominant superimposition of left and right eye perceptual states, or right-predominant superimposition of left and right eye perceptual states.

14. The method of claim 1, wherein said perceptual states comprise presence or absence of a form of rivalry, type of rivalry, response time of perceived change in rivalry, and conscious visual perception.

15. The method of claim 1, wherein the analysis of step (e) provides an indication of visual cognitive functioning, a monocular visual function, or a binocular visual function.

16. The method of claim 1, wherein perceptual state, stimulus property, and primary brain processing site are according to any portion of the table below

| Perceptual state | Stimulus property | Primary processing site |
| --- | --- | --- |
| Exclusive visibility | Static gratings | Early visual cortex V1 |
| | Objects | Para hippocampal place area (PPA) |
| | Faces | Fusiform area (FFA) |
| | Moving dots | Middle temporal (MT) area |
| Piecemeal perception | | Early visual cortex |
| Superimposed perception | | Binocular regions early visual cortex (Layer 4 V1, V2) |
| Interocularly grouped perception | | Early visual cortex V1 and V2 binocular |
| Traveling wave perception | | Early visual cortex V1. |

17. The method of claim 1 that is used as part of a healthcare diagnosis, a neuro-behavioral test, an ophthalmological test, an optometric test, a visual consciousness measurement, a visual function test, as a diagnostic test for a visual impairment, or as a test of an outcome of a vision-related treatment or surgery.

18. The method of claim 1, wherein said perception state in induced by viewing an interocular grouping, ambiguous figures, continuous flash suppression, an afterimage, or a face perception task.

19. The method of claim 1, wherein the method provides diagnosis, prognosis, or treatment outcome evaluation related to ophthalmic disorders such as cataract surgery, amblyopia, age-related macular degeneration, glaucoma, intraocular lens implantation, contact lens or spectacle prescription, and neurological disorders and damages such as traumatic brain injury, autism, attention deficit disorder, depression, bipolar disorder, or schizophrenia, Alzheimer disease, dyslexia.

20. A system for conducting a binocular rivalry test according to claim 1, the system comprising:

a stereoscopic or viewing device configured for displaying binocular images to a test subject;

an input device for input of responses from the test subject;

a data storage device configured for storing input data from the input device and test parameters; and an analysis device configured for analyzing one or more visual functions or perceptions of the subject.

21. The system of claim 20, wherein the stereoscopic viewing device comprises a head-mounted projection display, a 3D display system, a computer screen, or a display screen of a mobile device or tablet.

22. The system of claim 20, wherein the input device is a joystick, virtual reality flight stick, hand tracker, trackball, computer mouse, touchpad, or touch-sensitive screen.

23. The system of claim 20, wherein the data storage device and the analysis device are both present in a single computer, laptop, notebook, or mobile phone.

24. The system of claim 20, wherein the data storage device and the analysis device are at separate locations, the system further comprising a transmitter operative to send data from the data storage device to the analysis device.

25. The system of claim 20, further comprising a processor and memory comprising instructions for carrying out the method of claim 1.

* * * * *